(12) United States Patent
Gonzalez et al.

(10) Patent No.: US 9,534,261 B2
(45) Date of Patent: Jan. 3, 2017

(54) RECOVERING OFF-GAS FROM PHOTOBIOREACTOR

(71) Applicant: Pond Biofuels Inc., Scarborough (CA)

(72) Inventors: Jaime A. Gonzalez, Richmond Hill (CA); Max Kolesnik, Toronto (CA); Steven C. Martin, Toronto (CA)

(73) Assignee: Pond Biofuels Inc., Scarborough (CA)

( * ) Notice: Subject to any disclaimer, the term of this patent is extended or adjusted under 35 U.S.C. 154(b) by 0 days.

(21) Appl. No.: 13/659,693

(22) Filed: Oct. 24, 2012

(65) Prior Publication Data

US 2014/0113275 A1    Apr. 24, 2014

(51) Int. Cl.
*C12Q 3/00* (2006.01)
*C12M 1/00* (2006.01)

(52) U.S. Cl.
CPC ............... *C12Q 3/00* (2013.01); *C12M 21/02* (2013.01); *C12M 29/24* (2013.01)

(58) Field of Classification Search
None
See application file for complete search history.

(56) References Cited

U.S. PATENT DOCUMENTS

| | | |
|---|---|---|
| 2,658,310 A | 11/1953 | Cook |
| 2,715,795 A | 8/1955 | Pallotta et al. |
| 2,732,661 A | 1/1956 | Herman |
| 2,732,663 A | 1/1956 | Dewey |
| 2,815,607 A | 12/1957 | Schroeder |
| 2,854,792 A | 10/1958 | Juda |
| 3,224,143 A | 12/1965 | Tew et al. |
| 3,243,918 A | 4/1966 | Machiedo |
| 3,303,608 A | 2/1967 | Hannan |
| 3,403,471 A | 10/1968 | Clement et al. |
| 3,504,185 A | 3/1970 | Hitt et al. |
| 3,650,068 A | 3/1972 | Meyer et al. |
| 3,712,025 A | 1/1973 | Wallace |
| 3,763,824 A | 10/1973 | Schoon |
| 3,855,121 A | 12/1974 | Gough |
| 3,882,635 A | 5/1975 | Yamanaka et al. |

(Continued)

FOREIGN PATENT DOCUMENTS

| | | |
|---|---|---|
| CA | 2738397 | 11/2011 |
| CA | 2738410 | 11/2011 |

(Continued)

OTHER PUBLICATIONS

Britannica webpage—retrieved from retrieved from http://www.britannica.com/EBchecked/topic/108636/chemical-element/81245/The-atmosphere on May 13, 2013.*

(Continued)

*Primary Examiner* — Ralph Gitomer
*Assistant Examiner* — Trent Clarke
(74) *Attorney, Agent, or Firm* — Fish & Richardson P.C.

(57) ABSTRACT

There is provided a process for effecting growth of phototrophic biomass within the reaction zone of a photobioreactor, comprising, after effecting at least a reduction in the molar rate of supply of carbon dioxide to the reaction zone of the photobioreactor, supplying a gaseous photobioreactor exhaust, that includes diatomic (or molecular) oxygen being generated by photosynthesis effected within the reaction zone by the supplied carbon dioxide, to a combustion zone of a combustor.

20 Claims, 3 Drawing Sheets

(56) References Cited

U.S. PATENT DOCUMENTS

| | | |
|---|---|---|
| 3,959,923 A | 6/1976 | Selke |
| 3,986,297 A | 10/1976 | Ichimura et al. |
| 4,043,903 A | 8/1977 | Dor |
| 4,078,331 A | 3/1978 | Savins et al. |
| 4,084,346 A | 4/1978 | Stengel et al. |
| 4,087,936 A | 5/1978 | Savins et al. |
| 4,116,778 A | 9/1978 | Belousov et al. |
| 4,235,043 A | 11/1980 | Harasawa et al. |
| 4,253,271 A | 3/1981 | Raymond |
| 4,267,038 A | 5/1981 | Thompson |
| 4,297,000 A | 10/1981 | Fries |
| 4,324,068 A | 4/1982 | Anthony |
| 4,341,038 A | 7/1982 | Bloch et al. |
| 4,383,039 A | 5/1983 | Leavitt |
| 4,398,926 A | 8/1983 | Doshi |
| 4,417,415 A | 11/1983 | Cysewski et al. |
| 4,438,591 A | 3/1984 | Kessler |
| 4,442,211 A | 4/1984 | Greenbaum |
| 4,473,970 A | 10/1984 | Hills |
| 4,525,031 A | 6/1985 | Mori |
| 4,539,625 A | 9/1985 | Bornstein et al. |
| 4,595,405 A | 6/1986 | Agrawal et al. |
| 4,626,065 A | 12/1986 | Mori |
| 4,676,956 A | 6/1987 | Mori |
| 4,681,612 A | 7/1987 | O'Brien et al. |
| 4,724,214 A | 2/1988 | Mori |
| 4,781,843 A | 11/1988 | Baker et al. |
| 4,851,339 A | 7/1989 | Hills |
| 4,865,969 A | 9/1989 | Amen et al. |
| 4,869,017 A | 9/1989 | Bird et al. |
| 4,889,812 A | 12/1989 | Guinn et al. |
| 4,900,678 A | 2/1990 | Mori |
| 4,939,087 A | 7/1990 | Van Wie et al. |
| 4,952,511 A | 8/1990 | Radmer |
| 4,958,460 A | 9/1990 | Nielson et al. |
| 4,970,166 A | 11/1990 | Mori |
| 4,995,377 A | 2/1991 | Eiden |
| 5,040,486 A | 8/1991 | Pack |
| 5,081,036 A | 1/1992 | Familletti |
| 5,104,803 A | 4/1992 | Delente |
| 5,151,342 A | 9/1992 | Wiedemann |
| 5,151,347 A | 9/1992 | Delente et al. |
| 5,206,173 A | 4/1993 | Finn |
| 5,216,976 A | 6/1993 | Marinkovich |
| 5,330,915 A | 7/1994 | Wilson et al. |
| 5,334,497 A | 8/1994 | Inaba et al. |
| 5,358,858 A | 10/1994 | Chiang et al. |
| 5,424,209 A | 6/1995 | Kearney |
| 5,447,629 A | 9/1995 | Chaumont et al. |
| 5,534,404 A | 7/1996 | Laurance et al. |
| 5,534,417 A | 7/1996 | Arad et al. |
| 5,541,056 A | 7/1996 | Huntley et al. |
| 5,552,058 A | 9/1996 | Fanning |
| 5,558,984 A | 9/1996 | Young et al. |
| 5,565,108 A | 10/1996 | Dimesky et al. |
| 5,573,669 A | 11/1996 | Jensen |
| 5,578,472 A | 11/1996 | Ueda et al. |
| 5,614,378 A | 3/1997 | Yang et al. |
| 5,656,421 A | 8/1997 | Gebhard et al. |
| 5,659,977 A | 8/1997 | Jensen et al. |
| 5,670,046 A | 9/1997 | Kimmel |
| 5,682,709 A | 11/1997 | Erickson |
| 5,686,299 A | 11/1997 | Colwell et al. |
| 5,711,983 A | 1/1998 | Kyle et al. |
| 5,741,702 A | 4/1998 | Lorenz |
| 5,744,041 A | 4/1998 | Grove |
| 5,776,349 A | 7/1998 | Guelcher et al. |
| 5,843,762 A | 12/1998 | Moll |
| 5,846,435 A | 12/1998 | Haase |
| 5,846,816 A | 12/1998 | Forth |
| 5,851,398 A | 12/1998 | Adey |
| 5,871,952 A | 2/1999 | Ghirardi et al. |
| 5,882,849 A | 3/1999 | Leonard et al. |
| 5,897,997 A | 4/1999 | Louvel |
| 5,906,750 A | 5/1999 | Haase |
| 5,910,254 A | 6/1999 | Guelcher et al. |
| 5,912,113 A | 6/1999 | Nakamura et al. |
| 5,951,875 A | 9/1999 | Kanel et al. |
| 5,958,761 A | 9/1999 | Yogev et al. |
| 5,981,260 A | 11/1999 | Metz |
| 5,981,271 A | 11/1999 | Doucha et al. |
| 5,994,129 A | 11/1999 | Armstrong et al. |
| 6,000,551 A | 12/1999 | Kanel et al. |
| 6,022,701 A | 2/2000 | Boussiba et al. |
| 6,083,740 A | 7/2000 | Kodo et al. |
| 6,110,370 A | 8/2000 | Van Hille et al. |
| 6,120,690 A | 9/2000 | Haase |
| 6,128,135 A | 10/2000 | Stiles et al. |
| 6,140,365 A | 10/2000 | Kiy et al. |
| 6,156,561 A | 12/2000 | Kodo et al. |
| 6,174,720 B1 | 1/2001 | Oxley et al. |
| 6,228,332 B1 | 5/2001 | Dunn et al. |
| 6,237,284 B1 | 5/2001 | Erickson |
| 6,258,588 B1 | 7/2001 | Demetropoulos et al. |
| 6,284,453 B1 | 9/2001 | Siano |
| 6,287,852 B1 | 9/2001 | Kondo et al. |
| 6,299,774 B1 | 10/2001 | Ainsworth et al. |
| 6,348,347 B1 | 2/2002 | Hirabayashi et al. |
| 6,391,238 B1 | 5/2002 | Sato et al. |
| 6,477,841 B1 | 11/2002 | Yantovsky |
| 6,492,149 B1 | 12/2002 | Muller-Feuga |
| 6,509,188 B1 | 1/2003 | Trosch et al. |
| 6,524,486 B2 | 2/2003 | Borodyanski et al. |
| 6,571,735 B1 | 6/2003 | Wilkinson |
| 6,579,714 B1 | 6/2003 | Hirabayashi et al. |
| 6,602,703 B2 | 8/2003 | Dutil |
| 6,603,069 B1 | 8/2003 | Muhs et al. |
| 6,633,042 B1 | 10/2003 | Funken et al. |
| 6,648,949 B1 | 11/2003 | Der et al. |
| 6,667,171 B2 | 12/2003 | Bayless et al. |
| 6,673,532 B2 | 1/2004 | Rao |
| 6,673,592 B1 | 1/2004 | Wangt et al. |
| 6,709,862 B2 | 3/2004 | Curtis |
| 6,792,336 B1 | 9/2004 | Johnson et al. |
| 6,815,204 B2 | 11/2004 | Muller-Feuga et al. |
| 6,830,699 B2 | 12/2004 | Heidal |
| 6,851,387 B2 | 2/2005 | Untermeyer et al. |
| 6,858,430 B1 | 2/2005 | Reddy et al. |
| 6,887,692 B2 | 5/2005 | Paterek |
| 6,918,354 B2 | 7/2005 | Perriello |
| 6,929,942 B2 | 8/2005 | Moghe et al. |
| 6,936,459 B1 | 8/2005 | Venkatesh et al. |
| 6,989,252 B2 | 1/2006 | Melis et al. |
| 6,991,919 B1 | 1/2006 | Porter et al. |
| 7,001,519 B2 | 2/2006 | Linden et al. |
| 7,022,232 B2 | 4/2006 | Jensen |
| 7,033,823 B2 | 4/2006 | Chang |
| 7,056,725 B1 | 6/2006 | Lu |
| 7,135,308 B1 | 11/2006 | Bush et al. |
| 7,135,332 B2 | 11/2006 | Ouellette |
| 7,153,344 B2 | 12/2006 | Filippi et al. |
| 7,163,811 B2 | 1/2007 | Behrens et al. |
| 7,172,691 B2 | 2/2007 | Dunlop et al. |
| 7,176,017 B2 | 2/2007 | Parent et al. |
| 7,176,024 B2 | 2/2007 | Branson et al. |
| 7,183,074 B2 | 2/2007 | Chen et al. |
| 7,191,597 B2 | 3/2007 | Goldman |
| 7,198,940 B2 | 4/2007 | Vellinger et al. |
| 7,252,979 B2 | 8/2007 | Behrens et al. |
| 7,270,996 B2 | 9/2007 | Cannon et al. |
| 7,279,314 B2 | 10/2007 | Matsuo |
| 7,320,889 B2 | 1/2008 | Kahlert et al. |
| 7,331,178 B2 | 2/2008 | Goldman |
| 7,333,195 B2 | 2/2008 | Kreiß et al. |
| 7,392,615 B2 | 7/2008 | Lee |
| 7,425,441 B2 | 9/2008 | Broneske et al. |
| 7,435,581 B2 | 10/2008 | West |
| 7,449,313 B2 | 11/2008 | Rush |
| 7,479,226 B2 | 1/2009 | Dunlop et al. |
| 7,507,554 B2 | 3/2009 | Bush et al. |
| 7,507,579 B2 | 3/2009 | Boccazzi et al. |
| 7,510,864 B2 | 3/2009 | Krichevsky et al. |
| 7,514,247 B2 | 4/2009 | Rush |
| 7,531,350 B2 | 5/2009 | Shiau |

(56) References Cited

U.S. PATENT DOCUMENTS

| | | |
|---|---|---|
| 7,536,827 B2 | 5/2009 | Busch et al. |
| 7,566,551 B2 | 7/2009 | Zhang |
| 7,572,546 B2 | 8/2009 | Karamanev |
| 7,585,898 B2 | 9/2009 | Thothathri |
| 7,618,813 B2 | 11/2009 | Lee et al. |
| 7,632,414 B2 | 12/2009 | Hsu |
| 7,635,586 B2 | 12/2009 | West |
| 7,658,851 B2 | 2/2010 | Nelson et al. |
| 7,662,615 B2 | 2/2010 | Chang et al. |
| 7,662,616 B2 | 2/2010 | Hazlebeck et al. |
| 7,662,617 B2 | 2/2010 | Rush |
| 7,682,821 B2 | 3/2010 | Woods et al. |
| 7,687,161 B2 | 3/2010 | Karamanev |
| 7,687,261 B2 | 3/2010 | Hazlebeck et al. |
| 7,736,508 B2 | 6/2010 | Limcaco |
| 7,750,494 B1 | 7/2010 | Behrens et al. |
| 7,770,322 B2 | 8/2010 | Huntley et al. |
| 7,771,515 B2 | 8/2010 | Champagne et al. |
| 7,905,049 B2 | 3/2011 | Erd |
| 7,977,085 B2 | 7/2011 | Rispoli et al. |
| 8,262,776 B2 | 9/2012 | Hazlebeck et al. |
| 2002/0034817 A1 | 3/2002 | Henry et al. |
| 2002/0072109 A1 | 6/2002 | Bayless |
| 2002/0130076 A1 | 9/2002 | Merritt |
| 2002/0138454 A1 | 9/2002 | Gruenberg et al. |
| 2003/0044114 A1 | 3/2003 | Pelka |
| 2003/0153059 A1 | 8/2003 | Pilkington et al. |
| 2003/0155090 A1 | 8/2003 | Holmberg |
| 2003/0162273 A1 | 8/2003 | Melis et al. |
| 2003/0228684 A1 | 12/2003 | Burbidge et al. |
| 2004/0077036 A1 | 4/2004 | Thomas et al. |
| 2004/0191755 A1 | 9/2004 | Kemper et al. |
| 2004/0266622 A1 | 12/2004 | Park |
| 2005/0036932 A1 | 2/2005 | Takahashi et al. |
| 2005/0037480 A1 | 2/2005 | Chiueh |
| 2005/0044911 A1 | 3/2005 | Shimose |
| 2005/0064577 A1 | 3/2005 | Berzin |
| 2005/0186671 A1 | 8/2005 | Cannon et al. |
| 2005/0239182 A1 | 10/2005 | Berzin |
| 2005/0244957 A1 | 11/2005 | Stock |
| 2005/0260553 A1 | 11/2005 | Berzin |
| 2006/0019375 A1 | 1/2006 | Seidl et al. |
| 2006/0134598 A1 | 6/2006 | Kenney |
| 2006/0151402 A1 | 7/2006 | Hsu |
| 2006/0216818 A1 | 9/2006 | Amano |
| 2006/0223155 A1 | 10/2006 | Streeter |
| 2006/0258000 A1 | 11/2006 | Allen et al. |
| 2006/0275858 A1 | 12/2006 | Saucedo et al. |
| 2006/0281163 A1 | 12/2006 | Diz et al. |
| 2007/0010002 A1 | 1/2007 | Melkonian et al. |
| 2007/0015263 A1 | 1/2007 | Wumpelmann |
| 2007/0042487 A1 | 2/2007 | Cheshire |
| 2007/0048848 A1 | 3/2007 | Sears |
| 2007/0048859 A1 | 3/2007 | Sears |
| 2007/0054351 A1 | 3/2007 | Zhang |
| 2007/0092962 A1 | 4/2007 | Sheppard |
| 2007/0113474 A1 | 5/2007 | Everett et al. |
| 2007/0114186 A1 | 5/2007 | Dart et al. |
| 2007/0157614 A1 | 7/2007 | Goldman |
| 2007/0161095 A1 | 7/2007 | Gurin |
| 2007/0202582 A1 | 8/2007 | Bush et al. |
| 2007/0264708 A1 | 11/2007 | Bayless et al. |
| 2007/0269874 A1 | 11/2007 | Kosourov et al. |
| 2007/0275856 A1 | 11/2007 | Thothathri |
| 2008/0009055 A1 | 1/2008 | Lewnard |
| 2008/0028675 A1 | 2/2008 | Clifford et al. |
| 2008/0044887 A1 | 2/2008 | Maltezos et al. |
| 2008/0050800 A1 | 2/2008 | McKeeman et al. |
| 2008/0052987 A1 | 3/2008 | Busch et al. |
| 2008/0085536 A1 | 4/2008 | Nobles et al. |
| 2008/0086938 A1 | 4/2008 | Hazlebeck et al. |
| 2008/0096267 A1 | 4/2008 | Howard et al. |
| 2008/0113413 A1 | 5/2008 | Nobles et al. |
| 2008/0115500 A1 | 5/2008 | MacAdam et al. |
| 2008/0118964 A1 | 5/2008 | Huntley et al. |
| 2008/0131958 A1 | 6/2008 | Remmereit et al. |
| 2008/0138875 A1 | 6/2008 | Atehortua et al. |
| 2008/0155890 A1 | 7/2008 | Oyler |
| 2008/0160591 A1 | 7/2008 | Wilson et al. |
| 2008/0160593 A1 | 7/2008 | Oyler |
| 2008/0160597 A1 | 7/2008 | van et al. |
| 2008/0166779 A1 | 7/2008 | Thomas et al. |
| 2008/0176303 A1 | 7/2008 | Massie |
| 2008/0176304 A1 | 7/2008 | Lee |
| 2008/0178739 A1 | 7/2008 | Lewnard et al. |
| 2008/0182325 A1 | 7/2008 | Hobbs et al. |
| 2008/0210632 A1 | 9/2008 | Kruse |
| 2008/0213049 A1 | 9/2008 | Higgins et al. |
| 2008/0213868 A1 | 9/2008 | Fournier |
| 2008/0220486 A1 | 9/2008 | Weiss |
| 2008/0220489 A1 | 9/2008 | Offerman |
| 2008/0220515 A1 | 9/2008 | McCall |
| 2008/0241902 A1 | 10/2008 | Berry et al. |
| 2008/0254056 A1 | 10/2008 | Zhang |
| 2008/0268302 A1 | 10/2008 | McCall |
| 2008/0274494 A1 | 11/2008 | Kertz |
| 2008/0293132 A1 | 11/2008 | Goldman et al. |
| 2008/0299539 A1 | 12/2008 | Lee et al. |
| 2008/0299643 A1 | 12/2008 | Howard et al. |
| 2008/0303348 A1 | 12/2008 | Witters |
| 2008/0305539 A1 | 12/2008 | Hickey et al. |
| 2008/0311646 A1 | 12/2008 | Cong et al. |
| 2008/0318304 A1 | 12/2008 | Burton et al. |
| 2009/0004715 A1 | 1/2009 | Trimbur et al. |
| 2009/0011492 A1 | 1/2009 | Berzin |
| 2009/0017514 A1 | 1/2009 | Datta et al. |
| 2009/0023199 A1 | 1/2009 | Gal |
| 2009/0029445 A1 | 1/2009 | Eckelberry et al. |
| 2009/0035835 A1 | 2/2009 | Slavin |
| 2009/0047722 A1 | 2/2009 | Wilkerson |
| 2009/0047730 A1 | 2/2009 | Higgins et al. |
| 2009/0068715 A1 | 3/2009 | Ogaki et al. |
| 2009/0068727 A1 | 3/2009 | Karr |
| 2009/0075353 A1 | 3/2009 | Ogaki et al. |
| 2009/0077863 A1 | 3/2009 | Oyler |
| 2009/0077864 A1 | 3/2009 | Marker et al. |
| 2009/0081743 A1 | 3/2009 | Hazelbeck et al. |
| 2009/0081744 A1 | 3/2009 | Kastanek |
| 2009/0081748 A1 | 3/2009 | Oyler |
| 2009/0081770 A1 | 3/2009 | Srienc et al. |
| 2009/0087898 A1 | 4/2009 | Haase et al. |
| 2009/0104594 A1 | 4/2009 | Webb |
| 2009/0113790 A1 | 5/2009 | Erd |
| 2009/0117647 A1 | 5/2009 | Buddhi et al. |
| 2009/0126265 A1 | 5/2009 | Rasmussen et al. |
| 2009/0130706 A1 | 5/2009 | Berzin et al. |
| 2009/0130747 A1 | 5/2009 | Wen-Teng et al. |
| 2009/0134091 A1 | 5/2009 | Stephens et al. |
| 2009/0137013 A1 | 5/2009 | Schmid et al. |
| 2009/0137025 A1 | 5/2009 | Stephens et al. |
| 2009/0148927 A1 | 6/2009 | Schroeder et al. |
| 2009/0148931 A1 | 6/2009 | Wilkerson et al. |
| 2009/0151240 A1 | 6/2009 | Kayama et al. |
| 2009/0151241 A1 | 6/2009 | Dressler et al. |
| 2009/0155864 A1 | 6/2009 | Bauer et al. |
| 2009/0170184 A1 | 7/2009 | Shepherd et al. |
| 2009/0181438 A1 | 7/2009 | Sayre |
| 2009/0197322 A1 | 8/2009 | Goldman |
| 2009/0203067 A1 | 8/2009 | Eckerle et al. |
| 2009/0203115 A1 | 8/2009 | Busch et al. |
| 2009/0203116 A1 | 8/2009 | Bazaire |
| 2009/0205638 A1 | 8/2009 | Corcoran |
| 2009/0215155 A1 | 8/2009 | Cloud et al. |
| 2009/0221057 A1 | 9/2009 | Kennedy |
| 2009/0227003 A1 | 9/2009 | Blotsky et al. |
| 2009/0227456 A1 | 9/2009 | Hsu |
| 2009/0230040 A1 | 9/2009 | Limcaco |
| 2009/0232861 A1 | 9/2009 | Wright et al. |
| 2009/0233334 A1 | 9/2009 | Hildinger et al. |
| 2009/0249685 A1 | 10/2009 | Flowers et al. |
| 2009/0250401 A1 | 10/2009 | Kotelko et al. |
| 2009/0263889 A1 | 10/2009 | Wumpelmann |
| 2009/0269839 A1 | 10/2009 | Oyler |
| 2009/0275120 A1 | 11/2009 | Koch et al. |

(56) References Cited

U.S. PATENT DOCUMENTS

| | | |
|---|---|---|
| 2009/0286295 A1 | 11/2009 | Medoff et al. |
| 2009/0286296 A1 | 11/2009 | Hickey et al. |
| 2009/0291485 A1 | 11/2009 | Shigematsu et al. |
| 2009/0294354 A1 | 12/2009 | Theodore et al. |
| 2009/0298159 A1 | 12/2009 | Wu et al. |
| 2009/0305388 A1 | 12/2009 | Dressler et al. |
| 2009/0309515 A1 | 12/2009 | Crabb et al. |
| 2009/0317901 A1 | 12/2009 | Vance |
| 2009/0321349 A1 | 12/2009 | Offerman et al. |
| 2009/0324799 A1 | 12/2009 | Hartman et al. |
| 2009/0325253 A1 | 12/2009 | Ascon et al. |
| 2010/0003717 A1 | 1/2010 | Oyler |
| 2010/0003741 A1 | 1/2010 | Fromson |
| 2010/0005711 A1 | 1/2010 | McNeff |
| 2010/0011778 A1 | 1/2010 | Knight et al. |
| 2010/0018214 A1 | 1/2010 | Halachmi Katchanov |
| 2010/0021361 A1 | 1/2010 | Spencer |
| 2010/0021968 A1 | 1/2010 | Hu et al. |
| 2010/0028976 A1 | 2/2010 | Hu et al. |
| 2010/0028977 A1 | 2/2010 | Ng et al. |
| 2010/0034050 A1 | 2/2010 | Erb et al. |
| 2010/0035321 A1 | 2/2010 | Wilkerson et al. |
| 2010/0035343 A1 | 2/2010 | Cheng et al. |
| 2010/0043446 A1 | 2/2010 | Shirvanian et al. |
| 2010/0050502 A1 | 3/2010 | Wu et al. |
| 2010/0055765 A1 | 3/2010 | Frank |
| 2010/0062483 A1 | 3/2010 | Beliaev et al. |
| 2010/0068693 A1 | 3/2010 | Tsang et al. |
| 2010/0068779 A1 | 3/2010 | Wells et al. |
| 2010/0068791 A1 | 3/2010 | Merimon et al. |
| 2010/0068801 A1 | 3/2010 | Woods et al. |
| 2010/0071370 A1 | 3/2010 | O'Kane |
| 2010/0077654 A1 | 4/2010 | Wu et al. |
| 2010/0081122 A1 | 4/2010 | Shibuya et al. |
| 2010/0081177 A1 | 4/2010 | Schatz et al. |
| 2010/0081835 A1 | 4/2010 | Wu et al. |
| 2010/0093046 A1 | 4/2010 | Remmereit et al. |
| 2010/0093078 A1 | 4/2010 | Wang et al. |
| 2010/0099151 A1 | 4/2010 | Stroiazzo-Mougin et al |
| 2010/0099157 A1 | 4/2010 | Salvetzki |
| 2010/0099170 A1 | 4/2010 | Aswani |
| 2010/0101621 A1 | 4/2010 | Xu |
| 2010/0105125 A1 | 4/2010 | Haley |
| 2010/0105126 A1 | 4/2010 | Wright et al. |
| 2010/0105127 A1 | 4/2010 | Ginsburg |
| 2010/0105129 A1 | 4/2010 | Sanchez-Pina et al. |
| 2010/0107487 A1 | 5/2010 | Holland |
| 2010/0112649 A1 | 5/2010 | Willson et al. |
| 2010/0112700 A1 | 5/2010 | Shaaltiel et al. |
| 2010/0120134 A1 | 5/2010 | Gal |
| 2010/0139265 A1 | 6/2010 | Stroiazzo Mougin |
| 2010/0151558 A1 | 6/2010 | Alianell et al. |
| 2010/0159539 A1 | 6/2010 | Ascon et al. |
| 2010/0159567 A1 | 6/2010 | Kuehnle et al. |
| 2010/0159578 A1 | 6/2010 | Lacaze et al. |
| 2010/0159579 A1 | 6/2010 | Schuring et al. |
| 2010/0162620 A1 | 7/2010 | McCaffrey et al. |
| 2010/0167339 A1 | 7/2010 | Clayton et al. |
| 2010/0167381 A1 | 7/2010 | Woerlee et al. |
| 2010/0170149 A1 | 7/2010 | Keeler et al. |
| 2010/0173355 A1 | 7/2010 | Haase et al. |
| 2010/0173375 A1 | 7/2010 | Oyler |
| 2010/0184177 A1 | 7/2010 | Mitchell |
| 2010/0184194 A1 | 7/2010 | Nagnath |
| 2010/0189806 A1 | 7/2010 | Harper et al. |
| 2010/0190227 A1 | 7/2010 | Dauth et al. |
| 2010/0196995 A1 | 8/2010 | Weissman et al. |
| 2010/0203618 A1 | 8/2010 | Rispoli et al. |
| 2010/0210001 A1 | 8/2010 | Seyfried et al. |
| 2010/0210002 A1 | 8/2010 | McCaffrey et al. |
| 2010/0211812 A1 | 8/2010 | Bullen et al. |
| 2010/0216240 A1 | 8/2010 | Moolman et al. |
| 2010/0227368 A1 | 9/2010 | Steiner |
| 2010/0233786 A1 | 9/2010 | O'Connor |
| 2010/0233787 A1 | 9/2010 | Halachmi Katchanov |
| 2010/0233796 A1 | 9/2010 | Kurihara et al. |
| 2010/0267122 A1 | 10/2010 | Chinnasamy et al. |
| 2010/0273210 A1 | 10/2010 | Reddy |
| 2010/0297739 A1 | 11/2010 | Steiner et al. |
| 2010/0297749 A1 | 11/2010 | Aravanis et al. |
| 2011/0014683 A1 | 1/2011 | Vermaas et al. |
| 2011/0020913 A1 | 1/2011 | Rispoli et al. |
| 2011/0023565 A1 | 2/2011 | Yanik et al. |
| 2011/0027827 A1 | 2/2011 | Chi et al. |
| 2011/0070632 A1 | 3/2011 | Katoch et al. |
| 2011/0113681 A1 | 5/2011 | Mostertz et al. |
| 2011/0124091 A1 | 5/2011 | Lu et al. |
| 2011/0139409 A1 | 6/2011 | Erd |
| 2011/0159581 A1 | 6/2011 | Zhang et al. |
| 2011/0195473 A1 | 8/2011 | Wilhelm |
| 2011/0195493 A1 | 8/2011 | Stroiazzo-Mougin |
| 2011/0236958 A1 | 9/2011 | Wong |
| 2011/0287405 A1 | 11/2011 | Gonzalez et al. |
| 2012/0156669 A1 | 6/2012 | Gonzalez et al. |
| 2012/0202281 A1 | 8/2012 | Gonzalez et al. |
| 2012/0203714 A1 | 8/2012 | Gonzalez et al. |
| 2012/0276633 A1 | 11/2012 | Gonzalez et al. |
| 2014/0186931 A1 | 7/2014 | Gonzalez et al. |

FOREIGN PATENT DOCUMENTS

| | | |
|---|---|---|
| CA | 2738418 | 11/2011 |
| CA | 2738459 | 11/2011 |
| CA | 2738461 | 11/2011 |
| CA | 2738516 | 11/2011 |
| CN | 1668185 | 9/2005 |
| CN | 2749890 | 1/2006 |
| CN | 101139113 | 3/2008 |
| CN | 101254364 | 9/2008 |
| CN | 101356261 | 1/2009 |
| CN | 201381254 | 1/2010 |
| CN | 101648092 | 2/2010 |
| CN | 101669569 | 3/2010 |
| CN | 101696389 | 4/2010 |
| CN | 10326396 | 8/2013 |
| EP | 1072301 | 1/2001 |
| EP | 2422870 | 2/2012 |
| GB | 2458529 | 9/2009 |
| JP | 3076586 | 4/1991 |
| JP | 4084883 | 3/1992 |
| JP | 4287678 | 10/1992 |
| WO | WO 91/18108 | 11/1991 |
| WO | WO 98/00559 | 1/1998 |
| WO | WO 98/28081 | 7/1998 |
| WO | WO 98/28082 | 7/1998 |
| WO | WO 98/28083 | 7/1998 |
| WO | WO 98/28403 | 7/1998 |
| WO | WO 98/28404 | 7/1998 |
| WO | WO 99/01021 | 1/1999 |
| WO | WO 03/038348 | 5/2003 |
| WO | 03/094598 | 11/2003 |
| WO | WO 2005/006838 | 1/2005 |
| WO | WO 2006/020177 | 2/2006 |
| WO | 2007/047805 | 4/2007 |
| WO | WO 2007/070452 | 6/2007 |
| WO | WO 2007/134141 | 11/2007 |
| WO | WO 2008/008262 | 1/2008 |
| WO | WO 2008/028143 | 3/2008 |
| WO | 2008/079896 | 7/2008 |
| WO | WO 2008/089321 | 7/2008 |
| WO | WO 2008/128625 | 10/2008 |
| WO | WO 2008/156795 | 12/2008 |
| WO | WO 2008/156835 | 12/2008 |
| WO | WO 2009/015054 | 1/2009 |
| WO | WO 2009/018498 | 2/2009 |
| WO | WO 2009/094440 | 7/2009 |
| WO | WO 2009/134358 | 11/2009 |
| WO | WO 2009/142765 | 11/2009 |
| WO | 2010/010554 | 1/2010 |
| WO | WO 2010/002745 | 1/2010 |
| WO | WO 2010/009284 | 1/2010 |
| WO | WO 2010/011320 | 1/2010 |
| WO | WO 2010/021753 | 2/2010 |
| WO | WO 2010/034023 | 3/2010 |

(56) References Cited

FOREIGN PATENT DOCUMENTS

| WO | 2010/094015 | 8/2010 |
|---|---|---|
| WO | 2010/108049 | 9/2010 |
| WO | 2010/123943 | 10/2010 |
| WO | 2011/050578 | 5/2011 |
| WO | 2011/143749 | 11/2011 |

OTHER PUBLICATIONS

Berenguel et al. "Model predictive control of pH in tubular photobioreactors" *Journal of Process Control*, 2004 14, pp. 377-387.
Carvalho, A.P., et al., "Microalgal Reactors: A Review of Enclosed System Designs and Performances". Biotechnol. Prog., 2006, vol. 22, No. 6, pp. 1490-1506. ISSN: 87567938.
Cote, R. and Wright, R. "Resource Conservation and Industrial Symbiosis: Strategies for enhancing the environmental sustainability of the Keltic Petrochemical Cluster" Prepared by Eco-Efficiency Centre Dalhousie University, on Mar. 29, 2006 (Mar. 29, 2006), Retrieved on Apr. 19, 2012 (Apr. 19, 2012), Retrieved from the internet: <URL: http://eco-efficiency.management.dal.ca/Files/KelticPetrochemical Cluster.pdf.
Degen, et al. "A novel airlift photobioreactor with baffles for improved light utilization through the flashing light effect" *Journal of Biotechnology*, 2001, 92, pp. 89-94.
Eriksen "The technology of microalgal culturing". Biotechnol Lett., 2008, vol. 30, pp. 1525-1536. ISSN: 01415492.
Fernandez et al. "Airlift-driven external-loop tubular photobioreactors for outdoor production of microalgae assessment of design and performance" *Chemical Engineering Science* [Online], 2001, 56, 2721-2732.
Greenwell, et al., "Placing microalgae on the biofuels priority list: a review of the technological challenges" J. R. Soc. Interface 2010 7, 703-726 first published online Dec. 23, 2009 doi: 10.1098/rsif.2009.0322.
Hamilton, T. "CO2-eating algae turns cement maker green" The Star, Published on Mar. 18, 2010, Retrieved on Apr. 19, 2012, Retrieved from the internet: <URL: http://www.thestar.com/business/article/781426--co2-eating-algae-turns-cement-maker-green.
Hurst, T., "Canadian Cement Plant Becomes First to Capture CO2 in Algae—A Canadian company called Pond Biofuels is capturing CO2 emissions from a cement plant in algae-algae the company ultimately plans on using to make biofuel." Earth and Industry, Mar. 19, 2010, Retrieved on Apr. 19, 2012, Retrieved from the internet:<URL: http://earthandindustry.com/2010/03/canadian-cement-plant-becomes-first-to-capture-co2-in-algae.
International Search Report and Written Opinion; Application No. PCT/CA2011/001367; mailed Apr. 19, 2012; 22 pages.
International Search Report and Written Opinion; Application No. PCT/CA2011/000574; mailed Sep. 22, 2011; 21 pages.
International Search Report and Written Opinion; Application No. PCT/CA2012/000093; mailed May 23, 2012; 17 pages.
International Search Report and Written Opinion; Application No. PCT/CA2011/000097; mailed May 10, 2012; 10 pages.
International Search Report and Written Opinion; Application No. PCT/CA2011/000403; mailed Jul. 31 2012; 12 pages.
Ishida, M., et al., "$CO_2$ Recovery in a Power Plant with Chemical Looping Combustion". Energy Convers. Mgmt., 1997, vol. 38, Suppl., pp. S187-S192. ISSN: 01968904.
Janssen M et al., "Enclosed outdoor photobireactors: Light regime, photosynthetic efficiency, scale-up, and future prospects," Biotechnology and Bioengineering, vol. 81, Iss. 2, 2003, pp. 193-210.
Lee et al. "High density algal photobioreactors using light emitting diodes." *Biotech. BioEng.* [Online] 1994, 44. pp. 1161-1167.
Maeda, et al., "$CO_2$ fixation from the flue gas on coal-fired thermal power plant by microalgae". Energy Convers. Mgmt vol. 36, No. 6-9, pp. 717-720, 1995.

Masojidek et al. "A closed solar photobioreactor for cultivation of microalgae under supra-high irradiance basic design and performance" *Journal of Applied Phycology* [Online] 2003, 15, 239-248.
Matthijs et al. "Application of light emitting diodes in bioreactors: flashing light effects and energy economy in algal culture." *Biotechnol. Bioeng.* [Online] 2000, 50, pp. 98-107.
Meridian Planning Consultants Inc., "Bruce Energy Center Discussion Paper, Municipality of Kincardine" Prepared by Meridian Planning Consultants Inc. Jun. 2005 (Jun. 2005), Retrieved on Apr. 19, 2012 (Apr. 19, 2012), Retrieved from the internet: <URL: http://www.kincardine.net/publicdocs/documents/Bruce%20Energy%20C enter%20Discussion%20Paper1.pdf.
Negoro, et al., "Carbon Dioxide Fixation by Microalgae Photosynthesis Using Actual Flue Gas Discharged from a Boiler". Appl. Biochem. Biotechnol., 1993, vol. 39/40, pp. 643-653. ISSN: 02732289.
Pulz "Photobioreactors: production systems for phototrophic microorganisms". Appl. Microbiol. Biotechnol, 2001, vol. 57, pp. 287-293. ISSN: 01757598.
Putt "Algae as a Biodiesel Feedstock: A Feasibility Assessment" (Center for Microfibrous Materials Manufacturing, Department of Chemical Engineering, Auburn University, Alabama).
Stewart et al., "A Study of Methods of Carbon Dioxide Capture and Sequestration—The Sustainability of a Photosynthetic Bioreacter Approach," Energy Conversion and Management. 2005, 46:403-420.
Suh et al., "Photobioreactor Engineering: Design and Performance". Biotechnol. Bioprocess Eng., 2003, vol. 8, No. 6, pp. 313-321. ISSN: 12268372.
Wang, et al., "$CO_2$ bio-mitigation using microalgae". Appl. Microbiol. Biotechnol. 2008, vol. 79, pp. 709-718. ISSN: 01757598.
Yang, et al., "Progress in carbon dioxide separation and capture: A review". J.Env. Sci., 2008, vol. 20, pp. 14-27. ISSN: 10010742.
Zebib, "Microalgae Grown in Photobiorecators for Mass Production of Biofuel". Rutger University, Department of Bioenvironmental Engineering, Sep. 2008, 15 pages http://www.water.rutgers.edu/Educational_Programs/Senior%20Design2008/Algae%20to%20Energy%20Report.pdf.
Office Action issued in U.S. Appl. No. 13/659,714 on May 24, 2013, (17 pages).
Office Action issued in U.S. Appl. No 13/327,541 on Sep. 19, 2012, (22 pages).
Response to Office Action issued in U.S. Appl. No. 13/327,541 on Sep. 19, 2012, filed on Mar. 19, 2013 (20 pages).
Office Action issued in U.S. Appl. No. 13/327,541 on Jun. 27, 2013, (25 pages).
Office Action issued in U.S. Appl. No. 13/022,396 on Dec. 18, 2012, (19 pages).
Office Action issued in U.S. Appl. No. 13/021,489 on Mar. 18, 2013, (51 pages).
Response to Office Action issued in U.S. Appl. No. 13/021,489 on Mar. 18, 2013, filed on Sep. 18, 2013 (18 pages).
English Translation of the Second Office Action issued in CN 201280012900.7 on Jul. 21, 2015 (6 pages).
European Search Report issued in EP 12776555 on Dec. 22, 2014 (6 pages).
European Search Report issued in EP 11782806 on Aug. 1, 2014 (7 pages).
European Search Report issued in EP 11858246 on Sep. 17, 2014 (6 pages).
Final Office Action issued in U.S. Appl. No. 13/022,508 on Nov. 6, 2014, (10 pages).
Herzog et al., "Advanced Post-Combustion CO2 Capture" Clean Air Task Force, Apr. 2009, (39 pages).
Office Action issued in U.S. Appl. No. 13/095,490 on Oct. 8, 2014, (88 pages).
Office Action issued in U.S. Appl. No. 14/089,278 on Jan. 12, 2015, (16 pages).
Office Action issued in U.S. Appl. No. 13/021,489 on Dec. 4, 2014, (75 pages).
Office Action issued in U.S. Appl. No. 13/3271,541 on Sep. 19, 2014, (16 pages).

(56) References Cited

OTHER PUBLICATIONS

Response to Office Action issued in U.S. Appl. No. 13/095,490 on Oct. 8, 2014, filed on Mar. 9, 2015, 10 pages.
Response to Office Action issued in U.S. Appl. No. 13/327,541 on Sep. 19, 2014, filed on Mar. 19, 2015 (16 pages).
Response to Office Action issued in U.S. Appl. No. 13/022,508 on Nov. 6, 2014, filed on Apr. 6, 2015 (13 pages).
Chinese Office Action (with English translation) issued in CN 201180035594, on Jan. 16, 2015 (22 pages).
Chinese Office Action (with English Tranlation) issued in CN 2014091901006550, on Sep. 24, 2014 (25 pages).
Chinese Office Action (with English Translation) issued in CN 201280031706.3, on Jan. 9, 2015 (12 pages).
Taiwanese Office Action (with English Translation) issued in TW 10117390, Jun. 2, 2015 (19 pages).
Final Office Action issued in U.S. Appl. No. 13/021,489 on Nov. 29, 2013, (65 pages).
Hendershot et al., "Use Oxygen to Improve Combustion and Oxidation," American Institute of Chemical Engineers (AIChE), Chemical Engineering Progress, 57-60 (2010).
International Search Report and Written Opinion; Application No. PCT/CA2013/000908; mailed Jan. 23, 2014; 12 pages.
International Search Report and Written Opinion; Application No. PCT/CA2013/000904; mailed Feb. 7, 2014; 10 pages.
Kunjapur et al., "Photobioreactor Design for Commercial Biofuel Production from Microalgae," Ind. Eng. Chem. Res., 49:3516-3526 (2010).
Myklestad et al., "A photobioreactor with pH control: demonstration by growth of the marine diatom Skeletonema costatum," Journal of Plankton Research, 24(6):557-563 (2002).
Notice of Appeal filed in U.S. Appl. No. 13/327,521 filed on Dec. 20, 2013 (1 page).
Office Action issued in CN2014022101011280 on Feb. 26, 2014 with translation (20 pages).
Office Action issued in U.S. Appl. No. 13/021,489 on Mar. 18, 2013, (52 pages).
Office Action issued in U.S. Appl. No. 13/022,508 on Feb. 13, 2014 (13 pages).
Response to Office Action issued in U.S. Appl. No. 13/021,489 on Mar. 18, 2013, filed on Sep. 18, 2013 (20 pages).
Restriction Requirement issued in U.S. Appl. No. 13/095,490 on Apr. 11, 2014 (8 pages).
Shi et al., "Effects of the pH/pCO$_2$ control method on medium chemistry and phytoplankton growth," Biogeosciences, 6:1199-1207 (2009).
Sun et al., "An Experiment on Enclosed and Constant Culture of Marine Microalgae," Fisheries Science, 22(3):22-24 (2003).
Sun et al., "An Experiment on Enclosed and Constant Culture of Marine Microalgae," Fisheries Science, 22(3):22-24 (2003) (Translation), Abst. only.
Final Office Action issued in U.S. Appl. No. 13/095,490 on Jul. 8, 2015, 15 pages.
Response to Office Action issued in U.S. Appl. No. 14/089,278 on Jan. 12, 2015, filed on Jul. 13, 2015, 12 pages.
Final Office Action issued in U.S. Appl. No. 14/089,278 on Oct. 23, 2015, 20 pages.
Non-Final Office Action issued in U.S. Appl. No. 13/022,508 on Jul. 6, 2015, 13 pages.
Response to Office Action of Feb. 13, 2014 for U.S. Appl. No. 13/022,508 filed on Jul. 14, 2014, Fish & Richardson, 12 pages.
Response to Final Office Action of Nov. 27, 2013 for U.S. Appl. No. 13/021,489 filed on Oct. 20, 2014, 14 pages.
Final Office Action issued in U.S. Appl. No. 13/327,541 on Jul. 14, 2015, 15 pages.
Response to Office Action of Jun. 27, 2013 for U.S. Appl. No. 13/327,541 filed on May 27, 2014, 14 pages.
Non-final Office Action issued in U.S. Appl. No. 13/327,541 on Feb. 11, 2016, 15 pages.

\* cited by examiner

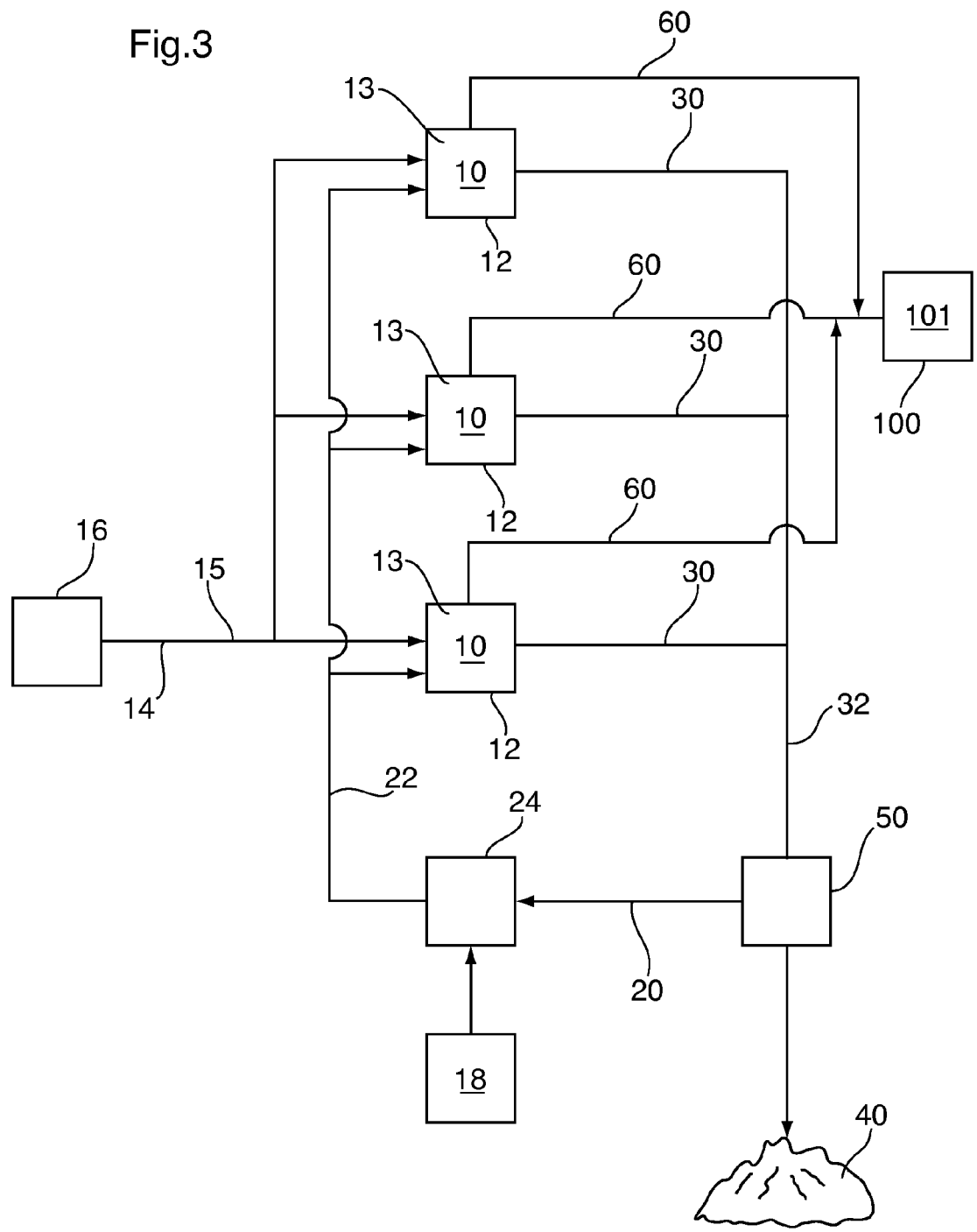

RECOVERING OFF-GAS FROM PHOTOBIOREACTOR

FIELD

The present disclosure relates to a process for growing biomass.

BACKGROUND

The cultivation of phototrophic organisms has been widely practised for purposes of producing a fuel source. Exhaust gases from industrial processes have also been used to promote the growth of phototrophic organisms by supplying carbon dioxide for consumption by phototrophic organisms during photosynthesis. By providing exhaust gases for such purpose, environmental impact is reduced and, in parallel a potentially useful fuel source is produced. Challenges remain, however, to render this approach more economically attractive for incorporation within existing facilities.

SUMMARY

In one aspect, there is provided a process for effecting growth of phototrophic biomass within the reaction zone of a photobioreactor, comprising, after effecting at least a reduction in the molar rate of supply of carbon dioxide to the reaction zone of the photobioreactor, supplying a gaseous photobioreactor exhaust, that includes diatomic (or molecular) oxygen being generated by photosynthesis effected within the reaction zone by the supplied carbon dioxide, to a combustion zone of a combustor.

BRIEF DESCRIPTION OF DRAWINGS

The process of the preferred embodiments of the invention will now be described with the following accompanying drawing:

FIG. 3 is a process flow diagram of another embodiment of the process.

DETAILED DESCRIPTION

Reference throughout the specification to "some embodiments" means that a particular feature, structure, or characteristic described in connection with some embodiments are not necessarily referring to the same embodiments. Furthermore, the particular features, structure, or characteristics may be combined in any suitable manner with one another.

Figure 1:
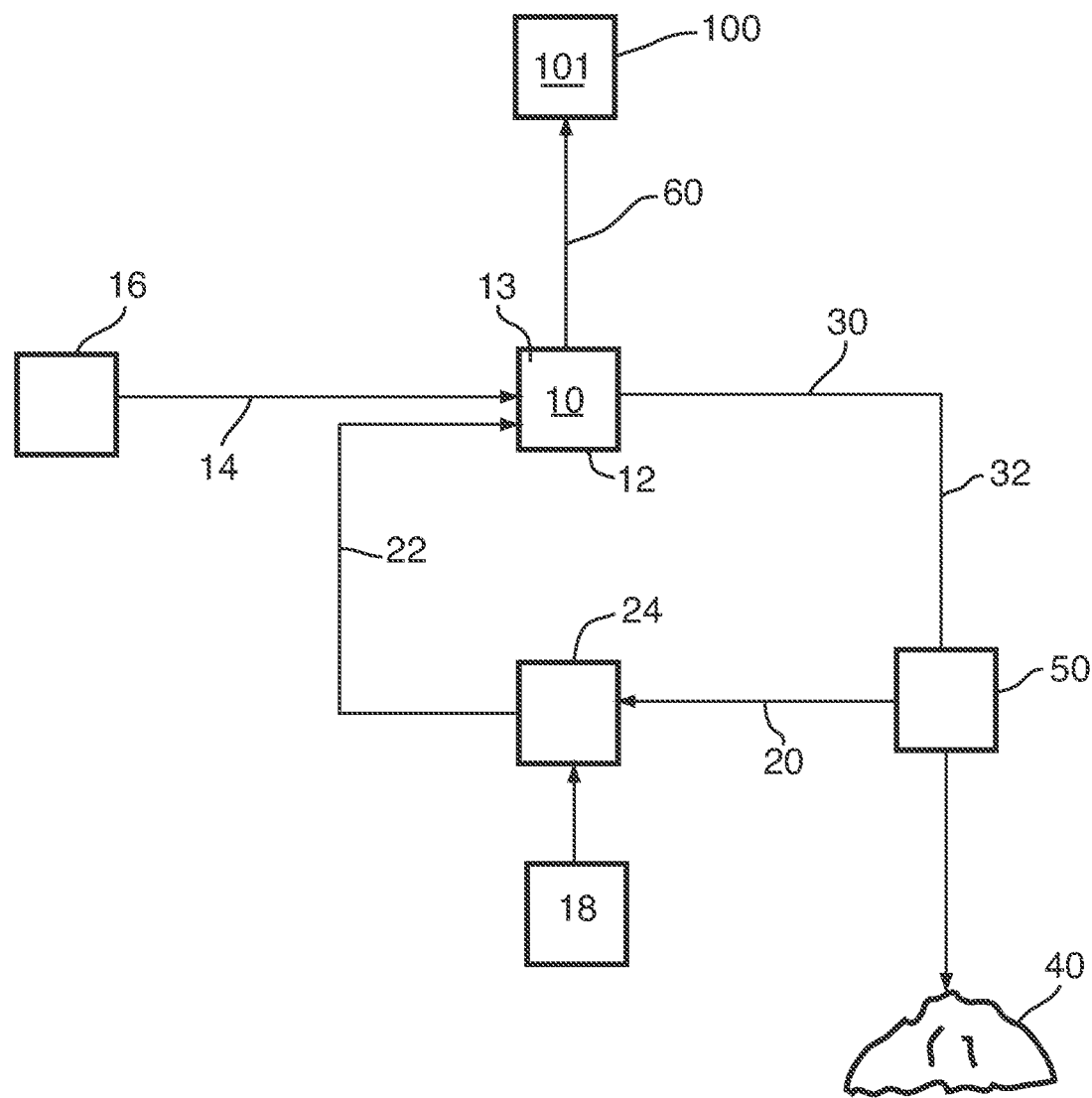
FIG. 1 is a process flow diagram of an embodiment of the process.

Referring to FIG. 1, there is provided a process of growing a phototrophic biomass within a reaction zone 10 of a photobioreactor 12.

The reaction zone 10 includes a reaction mixture that is operative for effecting photosynthesis upon exposure to photosynthetically active light radiation. The reaction mixture includes phototrophic biomass, carbon dioxide, and water. In some embodiments, the reaction zone includes phototrophic biomass and carbon dioxide disposed in an aqueous medium. Within the reaction zone 10, the phototrophic biomass is disposed in mass transfer communication with both of carbon dioxide and water.

"Phototrophic organism" is an organism capable of phototrophic growth in the aqueous medium upon receiving light energy, such as plant cells and micro-organisms. The phototrophic organism is unicellular or multicellular. In some embodiments, for example, the phototrophic organism is an organism which has been modified artificially or by gene manipulation. In some embodiments, for example, the phototrophic organism is an algae. In some embodiments, for example, the algae is micro algae.

"Phototrophic biomass" is at least one phototrophic organism. In some embodiments, for example, the phototrophic biomass includes more than one species of phototrophic organisms.

"Reaction zone 10" defines a space within which the growing of the phototrophic biomass is effected. In some embodiments, for example, pressure within the reaction zone is atmospheric pressure.

"Photobioreactor 12" is any structure, arrangement, land formation or area that provides a suitable environment for the growth of phototrophic biomass. Examples of specific structures which can be used is a photobioreactor 12 by providing space for growth of phototrophic biomass using light energy include, without limitation, tanks, ponds, troughs, ditches, pools, pipes, tubes, canals, and channels. Such photobioreactors may be either open, closed, partially closed, covered, or partially covered. In some embodiments, for example, the photobioreactor 12 is a pond, and the pond is open, in which case the pond is susceptible to uncontrolled receiving of materials and light energy from the immediate environments. In other embodiments, for example, the photobioreactor 12 is a covered pond or a partially covered pond, in which case the receiving of materials from the immediate environment is at least partially interfered with. The photobioreactor 12 includes the reaction zone 10 which includes the reaction mixture. In some embodiments, the photobioreactor 12 is configured to receive a supply of phototrophic reagents (and, in some of these embodiments, optionally, supplemental nutrients), and is also configured to effect discharge of phototrophic biomass which is grown within the reaction zone 10. In this respect, in some embodiments, the photobioreactor 12 includes one or more inlets for receiving the supply of phototrophic reagents and supplemental nutrients, and also includes one or more outlets for effecting the recovery or harvesting of biomass which is grown within the reaction zone 10. In some embodiments, for example, one or more of the inlets are configured to be temporarily sealed for periodic or intermittent time intervals. In some embodiments, for example, one or more of the outlets are configured to be temporarily sealed or substantially sealed for periodic or intermittent time intervals. The photobioreactor 12 is configured to contain the reaction mixture which is operative for effecting photosynthesis upon exposure to photosynthetically active light radiation. The photobioreactor 12 is also configured so as to establish photosynthetically active light radiation (for example, a light of a wavelength between about 400-700 nm, which can be emitted by the sun or another light source) within the photobioreactor 12 for exposing the phototrophic biomass. The exposing of the reaction mixture to the photosynthetically active light radiation effects photosynthesis and growth of the phototrophic biomass. In some embodiments, for example, the established light radiation is provided by an artificial light source 14 disposed within the photobioreactor 12. For example, suitable artificial lights sources include submersible fiber optics or light guides, light-emitting diodes ("LEDs"), LED strips and fluorescent lights. Any LED strips known in the art can be adapted for use in the photobioreactor 12. In the case of the submersible LEDs, in some embodiments, for example, energy sources include alternative energy sources, such as wind, photovoltaic cells, fuel cells, etc. to supply electricity to the LEDs. Fluorescent lights, external or internal to the photobioreactor 12, can be used as a back-up system. In some embodiments, for example, the established light is derived from a natural light source 16 which has been transmitted from externally of the photobioreactor 12 and through a transmission component. In some embodiments, for example, the transmission component is a portion of a containment structure of the photobioreactor 12 which is at least partially transparent to the photosynthetically active light radiation, and which is configured to provide for transmission of such light to the reaction zone 10 for receiving by the phototrophic biomass. In some embodiments, for example, natural light is received by a solar collector, filtered with selective wavelength filters, and then transmitted to the reaction zone 10 with fiber optic material or with a light guide. In some embodiments, for example, both natural and artificial lights sources are provided for effecting establishment of the photosynthetically active light radiation within the photobioreactor 12.

"Aqueous medium" is an environment that includes water. In some embodiments, for example, the aqueous medium also includes sufficient nutrients to facilitate viability and growth of the phototrophic biomass. In some embodiments, for example, supplemental nutrients may be included such as one of, or both of, $NO_X$ and $SO_X$. Suitable aqueous media are discussed in detail in: Rogers, L. J. and Gallon J. R. "Biochemistry of the Algae and Cyanobacteria," Clarendon Press Oxford, 1988; Burlew, John S. "Algal Culture: From Laboratory to Pilot Plant." Carnegie Institution of Washington Publication 600. Washington, D.C., 1961 (hereinafter "Burlew 1961"); and Round, F. E. The Biology of the Algae. St Martin's Press, New York, 1965; each of which is incorporated herein by reference). A suitable supplemental nutrient composition, known as "Bold's Basal Medium", is described in Bold, H. C. 1949, *The morphology of Chlamydomonas chlamydogama sp. nov. Bull. Torrey Bot. Club.* 76: 101-8 (see also Bischoff, H. W. and Bold, H. C. 1963. *Phycological Studies IV. Some soil algae from Enchanted Rock and related algal species*, Univ. Texas Publ. 6318: 1-95, and Stein, J. (ED.) *Handbook of Phycological Process, Culture process and growth measurements*, Cambridge University Press, pp. 7-24).

"Headspace" is that space within the photobioreactor 12 that is above the aqueous medium within the photobioreactor 12.

Carbon dioxide is supplied to the reaction zone 10 of the photobioreactor 12 for effecting the growth of the phototrophic biomass. In some embodiments, for example, the carbon dioxide being supplied to the photobioreactor is supplied by at least a fraction of the carbon dioxide-comprising exhaust material 14 being discharged by a carbon dioxide-comprising gaseous exhaust material producing process 16.

In some embodiments, for example, the carbon dioxide-comprising gaseous exhaust material 14 includes a carbon dioxide concentration of at least two (2) volume % based on the total volume of the carbon dioxide-comprising gaseous exhaust material 14. In some embodiments, for example, the carbon dioxide-comprising gaseous exhaust material 14 includes a carbon dioxide concentration of at least four (4) volume % based on the total volume of the carbon dioxide-comprising gaseous exhaust material 14. In some embodiments, for example, the gaseous exhaust material reaction 14 also includes one or more of $N_2$, $CO_2$, $H_2O$, $O_2$, $NO_R$, $SO_X$, CO, volatile organic compounds (such as those from unconsumed fuels) heavy metals, particulate matter, and ash. In some embodiments, for example, the carbon dioxide-comprising gaseous exhaust material 14 includes 30 to 60 volume % $N_2$, 5 to 25 volume % $O_2$, 2 to 50 volume % $CO_2$, and 0 to 30 volume % $H_2O$, based on the total volume of the carbon dioxide-comprising gaseous exhaust material 14. Other compounds may also be present, but usually in trace amounts (cumulatively, usually less than five (5) volume % based on the total volume of the carbon dioxide-comprising gaseous exhaust material 14).

In some embodiments, for example, the carbon dioxide-comprising gaseous exhaust material 14 includes one or more other materials, other than carbon dioxide, that are beneficial to the growth of the phototrophic biomass within the reaction zone 10. Materials within the gaseous exhaust material which are beneficial to the growth of the phototrophic biomass within the reaction zone 10 include $SO_X$, $NO_X$, and $NH_3$.

The carbon dioxide-comprising gaseous exhaust material producing process 16 includes any process which effects production and discharge of the carbon dioxide-comprising gaseous exhaust material 14. In some embodiments, for example, the carbon dioxide-comprising gaseous exhaust material producing process 16 is a combustion process. In some embodiments, for example, the combustion process is effected in a combustion facility. In some of these embodiments, for example, the combustion process effects combustion of a fossil fuel, such as coal, oil, or natural gas. For example, the combustion facility is any one of a fossil fuel-fired power plant, an industrial incineration facility, an industrial furnace, an industrial heater, or an internal combustion engine. In some embodiments, for example, the combustion facility is a cement kiln.

In some embodiments, for example, a supplemental nutrient supply 18 is supplied to the reaction zone 10 of the photobioreactor 12. In some embodiments, for example, the supplemental nutrient supply 18 is effected by a pump, such as a dosing pump. In other embodiments, for example, the supplemental nutrient supply 18 is supplied manually to the reaction zone 10. Nutrients within the reaction zone 10 are processed or consumed by the phototrophic biomass, and it is desirable, in some circumstances, to replenish the processed or consumed nutrients. A suitable nutrient composition is "Bold's Basal Medium", and this is described in Bold, H. C. 1949, *The morphology of Chlamydomonas chlamydogama sp. nov. Bull. Torrey Bot. Club.* 76: 101-8 (see also Bischoff, H. W. and Bold, H. C. 1963. *Phycological Studies IV. Some soil algae from Enchanted Rock and related species*, Univ. Texas Publ. 6318: 1-95, and Stein, J. (ED.) *Handbook of Phycological Process, Culture process and growth measurements*, Cambridge University Press, pp. 7-24). The supplemental nutrient supply 18 is supplied for supplementing the nutrients provided within the reaction zone, such as "Bold's Basal Medium", or one or more dissolved components thereof. In this respect, in some embodiments, for example, the supplemental nutrient supply 18 includes "Bold's Basal Medium". In some embodiments for example, the supplemental nutrient supply 18 includes one or more dissolved components of "Bold's Basal Medium", such as $NaNO_3$, $CaCl_2$, $MgSO_4$, $KH_2PO_4$, NaCl, or other ones of its constituent dissolved components.

In some embodiments, for example, the rate of supply of the supplemental nutrient supply 18 to the reaction zone 10 is controlled to align with a desired rate of growth of the phototrophic biomass in the reaction zone 10. In some embodiments, for example, regulation of nutrient addition is monitored by measuring any combination of pH, NO₃ concentration, and conductivity in the reaction zone 10.

In some embodiments, for example, a supply of the supplemental aqueous material supply 20 is effected to the reaction zone 10 of the photobioreactor 12, so as to replenish water within the reaction zone 10 of the photobioreactor 12. In some embodiments, for example, and as further described below, the supplemental aqueous material supply 20 effects the discharge of product from the photobioreactor 12 by displacement. For example, the supplemental aqueous material supply 20 effects the discharge of product from the photobioreactor 12 as an overflow.

In some embodiments, for example, the supplemental aqueous material is water or substantially water. In some embodiments, for example, the supplemental aqueous material supply 20 includes aqueous material that has been separated from a discharged phototrophic biomass-comprising product 32 by a separator 50 (such as a centrifugal separator). In some embodiments, for example, the supplemental aqueous material supply 20 is derived from an independent source (ie. a source other than the process), such as a municipal water supply.

In some embodiments, for example, the supplemental aqueous material supply 20 is supplied from a container that has collected aqueous material recovered from discharges from the process, such as aqueous material that has been separated from a discharged phototrophic biomass-comprising product.

In some embodiments, for example, the supplemental nutrient supply 18 is mixed with the supplemental aqueous material 20 in a mixing tank 24 to provide a nutrient-enriched supplemental aqueous material supply 22, and the nutrient-enriched supplemental aqueous material supply 22 is supplied to the reaction zone 10. In some embodiments, for example, the supplemental nutrient supply 18 is mixed with the supplemental aqueous material 20 within the container which has collected the discharged aqueous material. In some embodiments, for example, the supply of the nutrient-enriched supplemental aqueous material supply 18 is effected by a pump.

The reaction mixture disposed in the reaction zone 10 is exposed to photosynthetically active light radiation so as to effect photosynthesis. The photosynthesis effects growth of the phototrophic biomass.

In some embodiments, for example, light radiation is supplied to the reaction zone 10 for effecting the photosynthesis.

In some embodiments, for example, the light radiation is characterized by a wavelength of between 400-700 nm. In some embodiments, for example, the light radiation is in the form of natural sunlight. In some embodiments, for example, the light radiation is provided by an artificial light source. In some embodiments, for example, light radiation includes natural sunlight and artificial light.

In some embodiments, for example, the intensity of the supplied light radiation is controlled so as to align with the desired growth rate of the phototrophic biomass in the reaction zone 10. In some embodiments, regulation of the intensity of the provided light is based on measurements of the growth rate of the phototrophic biomass in the reaction zone 10. In some embodiments, regulation of the intensity of the provided light is based on the molar rate of supply of carbon dioxide to the reaction zone feed material 80.

In some embodiments, for example, the light radiation is supplied at predetermined wavelengths, depending on the conditions of the reaction zone 10. Having said that, generally, the light is provided in a blue light source to red light source ratio of 1:4. This ratio varies depending on the phototrophic organism being used. As well, this ratio may vary when attempting to simulate daily cycles. For example, to simulate dawn or dusk, more red light is provided, and to simulate mid-day condition, more blue light is provided. Further, this ratio may be varied to simulate artificial recovery cycles by providing more blue light.

It has been found that blue light stimulates algae cells to rebuild internal structures that may become damaged after a period of significant growth, while red light promotes algae growth. Also, it has been found that omitting green light from the spectrum allows algae to continue growing in the reaction zone 10 even beyond what has previously been identified as its "saturation point" in water, so long as sufficient carbon dioxide and, in some embodiments, other nutrients, are supplied.

With respect to artificial light sources, for example, suitable artificial light source 14 include submersible fiber optics, light-emitting diodes, LED strips and fluorescent lights. Any LED strips known in the art can be adapted for use in the process. In the case of the submersible LEDs, the design includes the use of solar powered batteries to supply the electricity. In the case of the submersible LEDs, in some embodiments, for example, energy sources include alternative energy sources, such as wind, photovoltaic cells, fuel cells, etc. to supply electricity to the LEDs.

With respect to those embodiments where the reaction zone 10 is disposed in a photobioreactor 12 which includes a tank, in some of these embodiments, for example, the light energy is provided from a combination of sources, as follows. Natural light source in the form of solar light is captured though solar collectors and filtered with custom mirrors that effect the provision of light of desired wavelengths to the reaction zone 10. The filtered light from the solar collectors is then transmitted through light guides or fiber optic materials into the photobioreactor 12, where it becomes dispersed within the reaction zone 10. In some embodiments, in addition to solar light, the light tubes in the photobioreactor 12 contains high power LED arrays that can provide light at specific wavelengths to either complement solar light, as necessary, or to provide all of the necessary light to the reaction zone 10 during periods of darkness (for example, at night). In some embodiments, with respect to the light guides, for example, a transparent heat transfer medium (such as a glycol solution) is circulated through light guides within the photobioreactor 12 so as to regulate the temperature in the light guides and, in some circumstances, provide for the controlled dissipation of heat from the light guides and into the reaction zone 10. In some embodiments, for example, the LED power requirements can be predicted and, therefore, controlled, based on trends observed with respect to the carbon dioxide-comprising gaseous exhaust material 14, as these observed trends assist in predicting future growth rate of the phototrophic biomass.

In some embodiments, the exposing of the reaction mixture to photosynthetically active light radiation is effected while the supplying of the carbon dioxide to the reaction zone 10 is being effected.

In some embodiments, for example, the growth rate of the phototrophic biomass is dictated by the available carbon dioxide within the reaction zone 10. In turn, this defines the nutrient, water, and light intensity requirements to maximize phototrophic biomass growth rate. In some embodiments, for example, a controller, e.g. a computer-implemented system, is provided to be used to monitor and control the operation of the various components of the process disclosed herein, including lights, valves, sensors, blowers, fans, dampers, pumps, etc.

In some embodiments, for example, reaction zone product 30 is discharged from the reaction zone 10. The reaction zone product 30 includes phototrophic biomass-comprising product 32. In some embodiments, for example, the phototrophic biomass-comprising product 32 includes at least a fraction of the contents of the reaction zone 10. In this respect, the discharge of the reaction zone product 30 effects harvesting of the phototrophic biomass 40.

In some embodiments, for example, the harvesting of the phototrophic biomass is effected by discharging the phototrophic biomass 32 from the reaction zone 10.

In some embodiments, for example, the discharging of the phototrophic biomass 32 from the reaction zone 10 is effected by displacement. In some of these embodiments, for example, the displacement is effected by supplying supplemental aqueous material supply 20 to the reaction zone 10. In some of these embodiments, for example, the displacement is an overflow. In some embodiments, for example, the discharging of the phototrophic biomass 32 from the reaction zone 10 is effected by gravity. In some embodiments, for example, the discharging of the phototrophic biomass 32 from the reaction zone 10 is effected by a prime mover that is fluidly coupled to the reaction zone 10.

In some embodiments, for example, the carbon dioxide-comprising gaseous exhaust material 14 is passed through the reaction zone 10 for effecting the photosynthesis such that the carbon dioxide-comprising gaseous exhaust material 14 becomes depleted in carbon dioxide, and such that production of a depleted carbon dioxide-comprising gaseous exhaust material is effected and exhausted into the headspace 13, and such that a gaseous headspace material, including the depleted carbon dioxide-comprising gaseous exhaust material, is disposed within the headspace 13. The photosynthesis effects generation of diatomic (or molecular) oxygen, such that the gaseous headspace material includes the generated diatomic (or molecular) oxygen.

Referring to FIG. 1, after effecting at least a reduction in the molar rate of supply of carbon dioxide to the reaction zone 10 of the photobioreactor 12, supplying a gaseous photobioreactor exhaust 60, that includes gaseous diatomic (or molecular) oxygen generated by photosynthesis effected within the reaction zone 10 by the supplied carbon dioxide, to a combustion zone 101 of a combustor 100.

Figure 2:
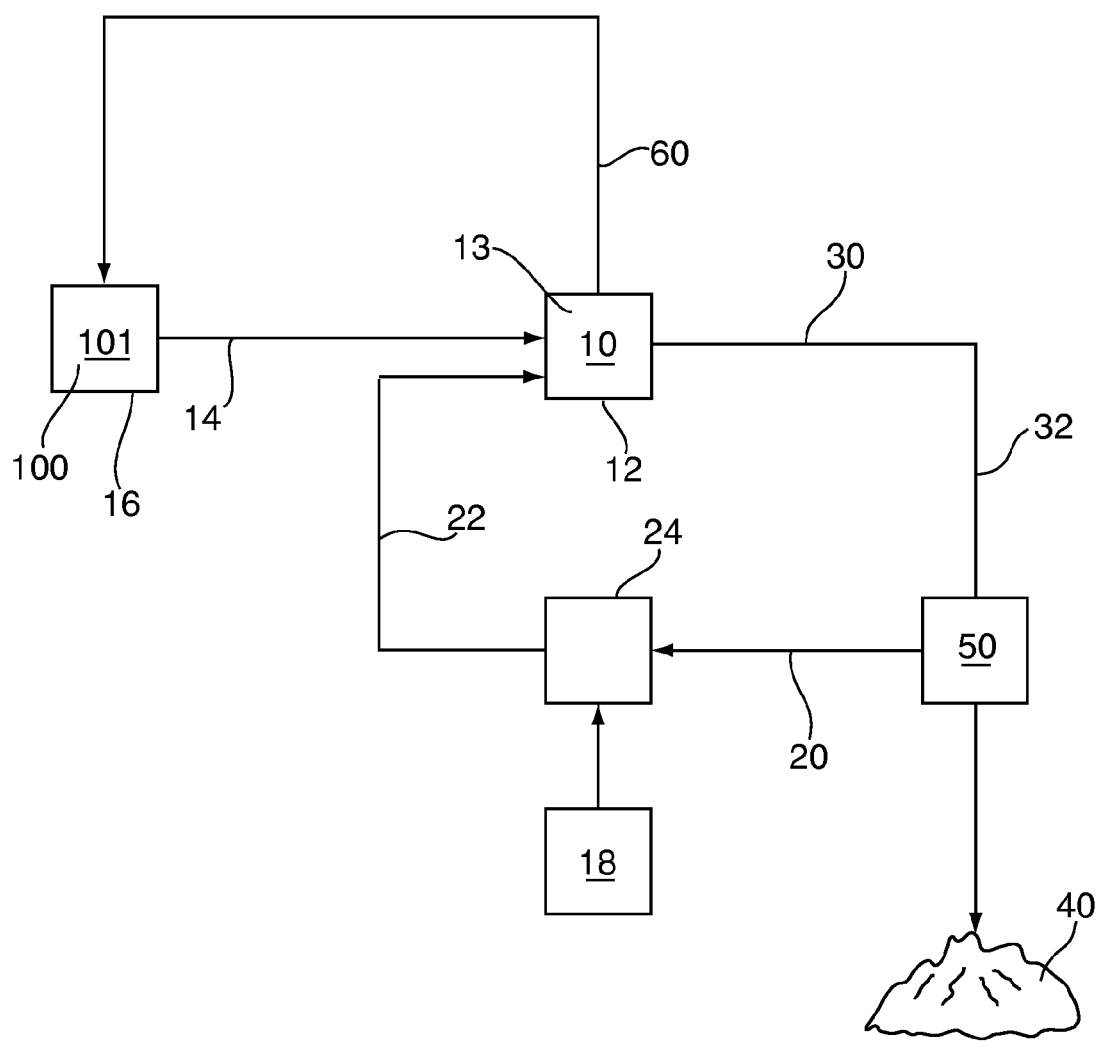
FIG. 2 is a process flow diagram of another embodiment of the process.

In some embodiments, for example, the combustor 100 is included within the unit operation that has been effecting at least a fraction of the supply of carbon dioxide to the reaction zone 10. In some of these embodiments, for example, and referring to FIG. 2, the carbon dioxide-comprising gaseous exhaust material producing process 16 includes the combustor 100.

In some embodiments, for example, the at least a reduction in the molar rate of supply of carbon dioxide to the reaction zone 10, that is effected, is at least a 5% reduction. In some embodiments, for example, the at least a reduction in the molar rate of supply of carbon dioxide to the reaction zone 10, that is effected, is at least a 10% reduction. In some embodiments, for example, the at least a reduction in the molar rate of supply of carbon dioxide to the reaction zone 10, that is effected, is at least a 25% reduction. In some embodiments, for example, the at least a reduction in the molar rate of supply of carbon dioxide to the reaction zone 10, that is effected, is at least a 50% reduction. In some embodiments, for example, the at least a reduction in the molar rate of supply of carbon dioxide to the reaction zone 10, that is effected, is a 100% reduction. In some embodiments, for example, the at least a reduction in the molar rate of supply of carbon dioxide to the reaction zone 10, that is effected, occurs over a time interval that is less than five (5) minutes in duration.

In some embodiments, for example, the process further includes effecting the at least a reduction in the molar rate of supply of carbon dioxide to the reaction zone 10.

In some embodiments, for example, the effecting at least a reduction in the molar rate of supply of carbon dioxide to the reaction zone 10 is defined by effecting a reduction in the molar rate of supply of carbon dioxide to the reaction zone 10, such that, after the reduction, supplying of carbon dioxide to the reaction zone 10 is effected at a reduced molar rate. In some of these embodiments, for example, the supplying a gaseous photobioreactor exhaust 60 to a combustion zone 101 of a combustor 100 is effected while the supplying of carbon dioxide to the reaction zone 10 is being effected at the reduced molar rate. In some of these embodiments, for example, the photosynthesis, that effects the generation of the diatomic (or molecular) oxygen of the photobioreactor exhaust 60 that is supplied to the combustion zone 101 of the combustor 100, is effected by the supplied carbon dioxide that is being supplied at the reduced molar rate to the reaction zone 10.

In some embodiments, for example, the effecting at least a reduction in the molar rate of supply of carbon dioxide includes, or is defined by, the suspension of the supply of carbon dioxide to the reaction zone 10, such that the supplying of carbon dioxide to the reaction zone 10 is suspended. In some of these embodiments, for example, the photosynthesis, that effects generation of the diatomic (or molecular) oxygen of the photobioreactor exhaust 60 that is supplied to the combustion zone 101 of the combustor 100, and which is being effected while the supplying of carbon dioxide to the reaction zone 10 is suspended, is effected by the supplied carbon dioxide that has been supplied to the reaction zone 10 prior to the suspending of the supply of carbon dioxide to the reaction zone 10.

In some embodiments, for example, the gaseous photobioreactor exhaust 60 includes at least a fraction of the gaseous headspace material, such that the supplying of the gaseous photobioreactor exhaust 60 to the combustion zone 101 of the combustor 100 includes discharging at least a fraction of the gaseous headspace material from the headspace 13 to the combustion zone 101 of the combustor 100.

In some embodiments, for example, the supplying includes purging at least a fraction of the gaseous headspace material from the headspace 13. In some embodiments, for example, the purging is effected by flowing a gaseous purge material through the headspace 13 so as to effect the discharging of at least a fraction of the gaseous headspace material to the combustion zone 101 of the combustor 100. In some embodiments, for example, prior to the flowing of the gaseous purge material through the headspace 13, the gaseous purge material is flowed through the reaction zone 10, for effecting mixing of materials within the reaction zone 10. In some embodiments, for example, the purge material includes, or is, air.

In some embodiments, for example, the supplying includes effecting evacuation of at least a fraction of the gaseous headspace material from the headspace 13, so as to effect the discharging of at least a fraction of the gaseous headspace material to the combustion zone 101 of the combustor 100.

In some embodiments, for example, prior to the supplying of the gaseous photobioreactor exhaust 60 to the combustion zone 101 of the combustor 100, and after the effecting at least a reduction in the molar rate of supply of carbon dioxide to the reaction zone 10, discharging at least a fraction of the gaseous headspace material (from the headspace 13) to a space other than that of the combustion zone 101 of the combustor 100. In some embodiments, for example, the space other than those of the combustion zone 101 is the atmosphere. In some embodiments, for example, the space other than those of the combustion zone 101 is a smokestack. In some of these embodiments, for example, the choice of the smokestack, as being the space other than those of the combustion zone 101, is dictated by environmental regulations. In some embodiments, the discharging at least a fraction of the gaseous headspace material (from the headspace 13) to a space other than that of the combustion zone 101 of the combustor 100, after the effecting at least a reduction in the molar rate of supply of carbon dioxide to the reaction zone 10, effects a reduction in the molar concentration of carbon dioxide of the gaseous headspace material within the headspace 13, such that the gaseous headspace material becomes of a quality that is suitable for effecting combustion of a fuel within the combustion zone 101 of the combustor 100, and thereby rendering it suitable for supplying to the combustion zone 101 of the combustor 100 as at least a portion of the photobioreactor exhaust 60.

In some embodiments, for example, the discharging at least a fraction of the gaseous headspace material (from the headspace 13) to a space other than that of the combustion zone 101 of the combustor 100, after the effecting at least a reduction in the molar rate of supply of carbon dioxide to the reaction zone 10, but prior to the supplying of the gaseous photobioreactor exhaust 60 to the combustion zone 101 of the combustor 100, includes purging at least a fraction of the gaseous headspace material from the headspace 13. In some embodiments, for example, the purging is effected by flowing a gaseous purge material through the headspace 13 so as to effect the discharging of at least a fraction of the gaseous headspace material to a space other than that of the combustion zone 101 of the combustor 100. In some embodiments, for example, prior to the flowing of the gaseous purge material through the headspace 13, the gaseous purge material is flowed through the reaction zone 10, for effecting mixing of materials within the reaction zone 10. In some embodiments, for example, the purge material includes, or is, air.

In some embodiments, for example, the discharging at least a fraction of the gaseous headspace material (from the headspace 13) to a space other than that of the combustor 100, after the effecting at least a reduction in the molar rate of supply of carbon dioxide to the reaction zone 10, but prior to the supplying of the gaseous photobioreactor exhaust 60 to the combustion zone 101 of the combustor 100, includes effecting evacuation of at least a fraction of the gaseous headspace material from the headspace 13, so as to effect the discharging of at least a fraction of the gaseous headspace material to a space other than that of the combustion zone 101 of the combustor 100.

In some embodiments, for example, the effecting at least a reduction in the molar rate of supply of carbon dioxide to the reaction zone 10 is defined by effecting a reduction in the molar rate of supply of carbon dioxide to the reaction zone 10, such that, after the reduction, supplying of carbon dioxide to the reaction zone 10 is effected at a reduced molar rate, and the discharging at least a fraction of the gaseous headspace material, to a space other than that of the combustion zone 101 of the combustor 100, is effected while the supplying of carbon dioxide to the reaction zone 10 is effected at a reduced molar rate.

In some embodiments, for example, the effecting at least a reduction in the molar rate of supply of carbon dioxide to the reaction zone 10 includes, or is defined by, the suspension of the supply of carbon dioxide to the reaction zone 10, such that the supplying of carbon dioxide to the reaction zone 10 is suspended, and the discharging at least a fraction of the gaseous headspace material, to a space other than that of the combustion zone 101 of the combustor 100, is effected while the supplying of carbon dioxide to the reaction zone 10 is suspended.

In some embodiments, for example, the supplying of the gaseous photobioreactor exhaust 60 to the combustion zone 101 of the combustor 100 is effected when the gaseous headspace material, within the headspace 13, is of a predetermined quality that is suitable for effecting combustion of a fuel. In some of these embodiments, for example, the supplying of the gaseous photobioreactor exhaust 60 to the combustion zone 101 of the combustor 100 is effected in response to sensing of the predetermined quality. In those embodiments where the sensing of the predetermined quality includes sensing of a gas concentration, for example, the sensing is effected by gas sensors.

In some of these embodiments, for example, the predetermined quality is defined as the molar concentration of carbon dioxide, within the gaseous headspace material within the headspace of the photobioreactor 12, that is less than, or equal to, a predetermined maximum concentration. In some embodiments, for example, the predetermined maximum concentration is 1.0 mol %, based on the total moles of the gaseous headspace material within the headspace 13. In some embodiments, for example, the predetermined maximum concentration is 0.7 mol %, based on the total moles of the gaseous headspace material within the headspace 13. In some embodiments, for example, the predetermined maximum concentration is 0.5 mol %, based on the total moles of the gaseous headspace material within the headspace 13.

In some embodiments, for example, the predetermined quality is defined as the molar concentration of diatomic (or molecular) oxygen, within the gaseous headspace material within the headspace of the photobioreactor 12, that is greater than, or equal to, a predetermined minimum concentration. In some embodiments, for example, the predetermined minimum concentration is 20 mol %, based on the total moles of the gaseous headspace material within the headspace 13. In some embodiments, for example, the predetermined minimum concentration is 25 mol %, based on the total moles of the gaseous headspace material within the headspace 13. In some embodiments, for example, the predetermined minimum concentration is 30 mol %, based on the total moles of the gaseous headspace material within the headspace 13. In some embodiments, for example, the predetermined minimum concentration is 40 mol %, based on the total moles of the gaseous headspace material within the headspace 13.

In some embodiments, for example, the predetermined quality is defined as the ratio of the molar concentration of diatomic (or molecular) oxygen, within the gaseous headspace material within the headspace of the photobioreactor 12, to the molar concentration of carbon dioxide, within the gaseous headspace material within the headspace of the photobioreactor 12, that is greater than, or equal to, a predetermined minimum value. In some embodiments, for example, the predetermined minimum value is 20. In some embodiments, for example, the predetermined minimum value is 25. In some embodiments, for example, the predetermined minimum value is 30. In some embodiments, for example, the predetermined minimum concentration is 40.

First Embodiment of Operating a Plurality of Photobioreactors

In some embodiments, for example, the process for effecting growth of phototrophic biomass within the reaction zone 10 of the photobioreactor 12 is effected while operating the photobioreactor 12 in combination with at least one other photobioreactor 12, such that a process for operating a plurality of photobioreactors 12 is provided. The plurality of photobioreactors 12 are operated so as to effect the growth of phototrophic biomass within each one of the plurality of photobioreactors 12.

In some of these embodiments, for example, and referring to FIG. 3, the effecting at least a reduction in the molar rate of supply of carbon dioxide to the reaction zone 10 of the photobioreactor 12 is effected by the suspension of the supplying of carbon dioxide to the reaction zone 10, and the process of operating the plurality of photobioreactors 12 includes, while a carbon dioxide-comprising gaseous exhaust material producing process 16 is effecting production of the carbon dioxide-comprising gaseous exhaust material 14, supplying at least a fraction of the produced carbon dioxide-comprising gaseous exhaust material 14 to a respective reaction zone 10 of each one of the phototobioreactors 12, in succession, wherein the at least a fraction of the produced carbon dioxide-comprising gaseous exhaust material being supplied defines a carbon dioxide-comprising gaseous exhaust supply 15.

Supplying the carbon dioxide-comprising gaseous exhaust supply 15 to a respective reaction zone 10 of each one of the phototobioreactors 12, in succession, means that the carbon dioxide-comprising gaseous exhaust supply 15 is supplied to a respective reaction zone of one of the photobioreactors 12 over a time interval, and at the completion of the time interval, the supplying of the carbon dioxide-comprising gaseous exhaust supply 15 to the respective reaction zone 10 of the one of the phototobioreactors is suspended, and after such suspension of the supplying, supplying of the carbon dioxide-comprising gaseous exhaust supply 15 to the respective reaction zone 10 of another one of the phototobioreactors is effected over a same or different time interval, and at the completion of such time interval, the supplying of the carbon dioxide-comprising gaseous exhaust supply 15 to the respective reaction zone 10 of the another one of the phototobioreactors is suspended. This continues until every one of the photobioreactors 12 is supplied by the carbon dioxide-comprising gaseous exhaust supply 15, independently, over a respective time interval. In some embodiments, for example, upon completion of the supplying of each one of the photobioreactors, in succession, by the carbon dioxide-comprising gaseous exhaust supply 15, a carbon dioxide-comprising exhaust supply cycle is thereby defined, and the carbon dioxide-comprising exhaust supply cycle is repeated at least one.

In some of these embodiments, for example, the carbon dioxide is being supplied by the carbon dioxide-comprising gaseous exhaust supply 15, at any given time during the process, to the reaction zone 10 of one of the photobioreactors 12. In some embodiments, for example, the supplying of the carbon dioxide-comprising gaseous exhaust supply 15 to a respective reaction zone 10 of each one of the phototobioreactors 12, in succession, independently, is effected over a respective time interval, and the supplying is continuous over that respective time interval. In some embodiments, for example, the supplying of the carbon dioxide-comprising gaseous exhaust supply 15 to a respective reaction zone 10 of each one of the phototobioreactors 12, in succession, independently, is effected over a respective time interval, and the supplying is semi-continuous or in intermittent pulses over that time interval.

After the suspension of the supplying of the carbon dioxide-comprising gaseous exhaust supply 15 to the reaction zone 10 of the one of the photobioreactors 12 being supplied by the carbon dioxide-comprising gaseous exhaust supply 15, and in accordance with any one of the embodiments described above, the supplying of the gaseous phototobioreactor exhaust 60 to the combustion zone 101 of the combustor 100 is effected.

In some embodiments, for example, for each one of the photobioreactors 12, growth of phototrophic biomass is being effected with the reaction zone 10.

In some embodiments, for example, the phototrophic biomass includes algae.

In some embodiments, for example, the supplying of the carbon dioxide-comprising gaseous exhaust supply 15 to a respective reaction zone 10 of each one of the phototobioreactors 12, in succession, is such that a carbon dioxide-comprising exhaust supply cycle is thereby defined. In some of these embodiments, for example, the carbon dioxide-comprising exhaust supply cycle is repeated at least once.

In some embodiments, for example, the carbon dioxide-comprising gaseous exhaust material supply 15 is defined by a fraction of the carbon dioxide-comprising gaseous exhaust material 14 being produced by the carbon dioxide-comprising gaseous exhaust material producing process 16, such that there is a remainder of the produced carbon dioxide-comprising gaseous exhaust material, and at least a fraction of the remainder of the produced carbon dioxide-comprising gaseous exhaust material 15 is being otherwise supplied to a respective reaction zone 10 of at least one of the photobioreactors 12. "Otherwise supplied" means that such fraction of the remainder is not included within the fraction that is being supplied by the produced carbon dioxide-comprising gaseous exhaust material 15 to the respective reaction zone 10 of each one of the photobioreactors 12, in succession.

In some embodiments, for example, the carbon dioxide-comprising gaseous exhaust material supply 15 being supplied is defined by the entire, or substantially the entire, carbon dioxide-comprising gaseous exhaust material 14 being produced by the carbon dioxide-comprising gaseous exhaust material producing process 16.

In some embodiments, for example, the supplying of the carbon dioxide-comprising gaseous exhaust supply 15 to a respective reaction zone 10 of each one of the phototobioreactors 12, in succession, independently, is effected over a respective time interval that is of a predetermined time duration.

In some embodiments, for example, the supplying of the carbon dioxide-comprising gaseous exhaust supply 15 to a respective reaction zone 10 of each one of the phototobioreactors 12, in succession, independently, is effected over a respective time interval whose duration is the same or substantially the same.

In some embodiments, for example, while the pH, within the reaction zone 10 of the photobioreactor 12, which is being supplied by the carbon dioxide-comprising gaseous exhaust supply 15 ("the supplied photobioreactor"), is disposed above a predetermined low pH limit, the time interval over which the carbon dioxide-comprising gaseous exhaust supply 15 is being supplied to the supplied photobioreactor 12 is of a predetermined duration, and after the pH, within the reaction zone 10 of the supplied photobioreactor 12, is disposed below the predetermined low pH limit, the supplying of the carbon dioxide-comprising gaseous exhaust supply 15, to the reaction zone 10 of the supplied photobioreactor 12, becomes suspended such that the time interval, over which the carbon dioxide-comprising gaseous exhaust supply 15 is supplied to the reaction zone 10 of the supplied photobioreactor 12, is less than the predetermined duration. In some of these embodiments, for example, the suspension of the supplying of the carbon dioxide-comprising gaseous exhaust supply 15 to the supplied photobioreactor 12 is effected in response to detection of the pH, within the reaction zone 10 of the supplied photobioreactor 12, is disposed below the predetermined low pH limit.

In those embodiments where the supplying of the carbon dioxide-comprising gaseous exhaust supply 15 to a respective reaction zone 10 of each one of the phototobioreactors 12, in succession, is such that a carbon dioxide-comprising exhaust supply cycle is thereby defined, wherein the carbon dioxide-comprising exhaust supply cycle is repeated at least once, and after at least one cycle has been completed and a subsequent cycle has yet to begin or has been partially completed, upon the completion of the time interval, over which the supplying of the carbon dioxide-comprising gaseous exhaust supply 15 to the respective reaction zone 10 of any one of the photobioreactors 12 is effected, when the pH, within the reaction zone 10 of the following photobioreactor 12 to be supplied within the current cycle or the next cycle (if the photobioreactor 12, to whose reaction zone the supplying of the carbon dioxide-comprising gaseous exhaust supply 15 has been effected over the time interval which has been completed, is the last photobioreactor to be supplied within the current cycle, the following photobioreactor is the first photobioreactor to be supplied within the next cycle), becomes disposed below a predetermined low pH limit, the supplying of the carbon dioxide-comprising gaseous exhaust supply 15, to the reaction zone 10 of the following photobioreactor 12 is skipped for the current cycle, such that a bypassed photobioreactor is defined. In some embodiments, for example, the discharging of the gaseous photobioreactor exhaust 60 from the bypassed photobioreactor, and its supplying to the combustion zone 101 of the combustor 100, is effected or continues to be effected.

With respect to those embodiments where pH within the reaction zone 10 is sensed or detected, or where it is implicit that pH within the reaction zone 10 must be sensed or detected, a pH sensor is provided for sensing pH within the reaction zone 10. The pH sensor may be disposed for directly or indirectly sensing pH within the reaction zone 10. For example, in some embodiments, indirect sensing of pH within the reaction zone includes sensing of pH within the reaction zone product 60 being discharged from the reaction zone 10. The sensed pH is then transmitted to a controller. The controller compares the sensed pH to a predetermined value, and then determines what, if any, other action is to be taken, such as manipulating valves to reconfigure the supplying of the photobioreactors 12 by the carbon dioxide-comprising gaseous exhaust material supply 15.

Second Embodiment of Operating a Plurality of Photobioreactors

In some embodiments, for example, a further process for operating a plurality of photobioreactors is provided. In such embodiments, the process for operating a plurality of photobioreactors includes, while a carbon dioxide-comprising gaseous exhaust material producing process 16 is effecting production of carbon dioxide-comprising gaseous exhaust material 14, and a carbon dioxide-comprising gaseous exhaust material supply 15, including at least a fraction of the produced carbon dioxide-comprising gaseous exhaust material 14, is supplied to a respective reaction zone 10 of one or more of the photobioreactors 12 ("the supplied photobioreactor(s)"), after the pH, within the reaction zone 10, of any one of the one or more supplied photobioreactor(s) 12, becomes disposed below a predetermined low pH limit, such that a low pH-disposed photobioreactor 12 is defined, at least a fraction of the carbon dioxide-comprising gaseous exhaust material supply 15, being supplied to the low pH-disposed photobioreactors, is diverted to a respective reaction zone 10 of each one of at least another one of the photobioreactors 12, for effecting supply of the diverted carbon dioxide-comprising gaseous exhaust material supply to the respective reaction zone 10 of each one of the at least another one of the photobioreactors 12. The diversion of the at least a fraction of the carbon dioxide-comprising gaseous exhaust material supply to the respective reaction zone 10 of the at least another one of the photobioreactors 12, is such that there is a reduction in the molar rate of supply of carbon dioxide being supplied to the reaction zone of the low pH-disposed photobioreactor 12, and an increase in the molar rate of supply of carbon dioxide being supplied to the respective reaction zone of each one of the at least another one of the photobioreactors 12.

After the reduction in the molar rate of supply of carbon dioxide being supplied to the reaction zone of the low pH-disposed photobioreactor 12 has been effected, and in accordance with any one of the embodiments described above, the supplying of the gaseous photobioreactor exhaust 60, from the low pH-disposed photobioreactor 12, to the combustion zone 101 of the combustor 100, is effected.

In some of these embodiments, for example, for each one of the photobioreactors 12, growth of phototrophic biomass is being effected within the reaction zone 10.

In some of these embodiments, for example, the phototrophic biomass includes algae.

In some embodiments, for example, the diverting of the at least a fraction of the carbon dioxide-comprising gaseous exhaust material supply 15, being supplied to the reaction zone of the low pH-disposed photobioreactor, to a respective reaction zone 10 of at least another one of the photobioreactors 12, is effected in response to detection of the pH, within the reaction zone 10 of the low pH-disposed photobioreactor 12, becoming disposed below the predetermined low pH limit.

In some of these embodiments, for example, the respective reaction zone of each one of the at least another one of the photobioreactors 12, to which the at least a fraction of the carbon dioxide-comprising gaseous exhaust material supply 15, being supplied to the reaction zone 10 of the low pH-disposed photobioreactor 12, is diverted, includes a pH that is greater than the predetermined low pH.

In some embodiments, for example, the respective reaction zone 10 of each one of the at least another one of the photobioreactors 12, to which the at least a fraction of the carbon dioxide-comprising gaseous exhaust material supply 15, being supplied to the reaction zone 10 of the low pH-disposed photobioreactor 12, is diverted, includes a pH that is greater than or equal to the pH of the respective reaction zone 10 of every other one of the photobioreactors 12, other than the low pH-disposed photobioreactor 12.

In some embodiments, for example, the entire, or substantially the entire, carbon dioxide-comprising gaseous exhaust material supply 15, being supplied to the reaction zone 10 of the low pH-disposed photobioreactor 12, is diverted to a respective reaction zone 10 of at least another one of the photobioreactors 12, after the pH, within the respective reaction zone 10 of the low pH-disposed photobioreactor 12, becomes disposed below a predetermined low pH limit. In this respect, in such embodiments, for example, the supplying of the carbon dioxide-comprising gaseous exhaust material supply 15, to the respective reaction zone 10 of the low pH-disposed photobioreactor 12, becomes suspended after the pH, within the respective reaction zone 10 of the low pH-disposed photobioreactor 12, becomes disposed below a predetermined low pH limit. In some of these embodiments, for example, the diverting of the entire, or substantially the entire, carbon dioxide-comprising gaseous exhaust material supply 15, being supplied to the reaction zone 10 of the low pH-disposed photobioreactor 12, to the respective reaction zone 10 of each one of the at least another one of the photobioreactors 12, is effected in response to detection of the pH, within the reaction zone 10 of the low pH-disposed photobioreactor 12, becoming disposed below the predetermined low pH limit.

With respect to those embodiments where pH within the reaction zone 10 is sensed or detected, or where it is implicit that pH within the reaction zone 10 must be sensed or detected, a pH sensor is provided for sensing pH within the reaction zone 10. The pH sensor may be disposed for directly or indirectly sensing pH within the reaction zone 10. For example, in some embodiments, indirect sensing of pH within the reaction zone includes sensing of pH within the reaction zone product 60 being discharged from the reaction zone 10. The sensed pH is then transmitted to a controller. The controller compares the sensed pH to a predetermined value, and then determines what, if any, other action is to be taken, such as manipulating valves to reconfigure the supplying of the photobioreactors 12 by the carbon dioxide-comprising gaseous exhaust material supply 15.

Third Embodiment of Operating a Plurality of Photobioreactors

In some embodiments, for example, a further process for operating a plurality of photobioreactors is provided. In such embodiments, the process for operating a plurality of photobioreactors includes, while a carbon dioxide-comprising gaseous exhaust material producing process 16 is effecting production of carbon dioxide-comprising gaseous exhaust material 14, and a carbon dioxide-comprising gaseous exhaust material supply 15, including at least a fraction of the produced carbon dioxide-comprising gaseous exhaust material 14, is supplied to a respective reaction zone 10 of one or more photobioreactors 12 ("the supplied photobioreactor(s)"), after the pH, within the reaction zone 10, of any one of the one or more supplied photobioreactor(s) 12, becomes disposed in excess of a predetermined maximum pH limit, such that a high pH-disposed photobioreactor 12 is defined, at least a fraction of the carbon dioxide-comprising gaseous exhaust material supply 15 being supplied to the respective reaction zone of each one of at least another one of the photobioreactors 12, whose reaction zone 10 includes a pH that is less than the pH within the reaction zone of the high pH-disposed photobioreactor, is diverted to the high pH-disposed photobioreactor 12, for effecting supply of the diverted carbon dioxide-comprising gaseous exhaust material supply to the reaction zone 10 of the high pH-disposed photobioreactor 12. In some of these embodiments, for example, the respective reaction zone of each one of the at least another one of the photobioreactors 12, from which the at least a fraction of the carbon dioxide-comprising gaseous exhaust material supply 15 is diverted to the reaction zone of the high pH-disposed photobioreactor 12, includes a pH that is less than or equal to the pH of the respective reaction zone 10 of every other one of the photobioreactors 12.

The diversion of the at least a fraction of the carbon dioxide-comprising gaseous exhaust material supply to the reaction zone 10 of the high pH-disposed photobioreactor 12, is such that there is a reduction in the molar rate of supply of carbon dioxide being supplied to the respective reaction zone of each one of the at least another one of the photobioreactors 12 (from which the at least a fraction of the carbon dioxide-comprising gaseous exhaust material supply is diverted), and an increase in the molar rate of supply of carbon dioxide being supplied to the reaction zone of the high pH-disposed photobioreactor 12.

After the reduction in the molar rate of supply of carbon dioxide being supplied to the respective reaction zone of each one of the at least another one of the photobioreactors has been effected, and in accordance with any one of the embodiments described above, the supplying of the gaseous photobioreactor exhaust 60, from such photobioreactors, to the combustion zone 101 of the combustor 100, is effected.

With respect to those embodiments where pH within the reaction zone 10 is sensed or detected, or where it is implicit that pH within the reaction zone 10 must be sensed or detected, a pH sensor is provided for sensing pH within the reaction zone 10. The pH sensor may be disposed for directly or indirectly sensing pH within the reaction zone 10. For example, in some embodiments, indirect sensing of pH within the reaction zone includes sensing of pH within the reaction zone product 60 being discharged from the reaction zone 10. The sensed pH is then transmitted to a controller. The controller compares the sensed pH to a predetermined value, and then determines what, if any, other action is to be taken, such as manipulating valves to reconfigure the supplying of the photobioreactors 12 by the carbon dioxide-comprising gaseous exhaust material supply 15.

While this invention has been described with reference to illustrative embodiments and examples, the description is not intended to be construed in a limiting sense. Thus, various modifications of the illustrative embodiments, as well as other embodiments of the invention, will be apparent to persons skilled in the art upon reference to this description. It is therefore contemplated that the appended claims will cover any such modifications or embodiments. Further, all of the claims are hereby incorporated by reference into the description of the preferred embodiments.

The invention claimed is:

1. A process for effecting growth of phototrophic biomass within a reaction zone of a photobioreactor, comprising:
 generating carbon dioxide-comprising gaseous exhaust material from a carbon dioxide-comprising gaseous exhaust material producing process;
 supplying the carbon dioxide-comprising gaseous exhaust material to the reaction zone of a photobioreactor such that carbon dioxide is thereby supplied to the reaction zone;
 producing a gaseous headspace material within a headspace of the photobioreactor with gaseous photobioreactor exhaust produced by photosynthesis within the reaction zone; and
 after at least reducing the rate of supply of carbon dioxide to the reaction zone of the photobioreactor:

(i) discharging at least a fraction of the gaseous headspace material to a space other than that of a combustion zone of a combustor, wherein the discharging effects a reduction in the molar concentration of carbon dioxide of the gaseous headspace material, such that the gaseous headspace material becomes of a quality that is suitable for effecting combustion of a fuel within the combustion zone of a combustor; and (ii) after the discharging in (i), discharging the gaseous photobioreactor exhaust to the combustion zone of the combustor.

2. The process as claimed in claim 1;
wherein reducing the rate of supply of carbon dioxide to the reaction zone is defined by reducing the supply of carbon dioxide to the reaction zone, such that, after the reduction, supplying of carbon dioxide to the reaction zone is effected at a reduced molar rate, and the discharging at least a fraction of a gaseous headspace material to a space other than that of the combustion zone of the combustor is effected while the supplying of carbon dioxide to the reaction zone is effected at a reduced molar rate.

3. The process as claimed in claim 2;
wherein the discharging of the gaseous photobioreactor exhaust to the combustion zone of the combustor is effected when the gaseous headspace material, within the headspace, is of a predetermined quality that is suitable for effecting combustion of a fuel.

4. The process as claimed in claim 3;
wherein the predetermined quality is defined as the molar concentration of carbon dioxide, within the gaseous headspace material within the headspace of the photobioreactor, that is less than, or equal to, 1.0 mol %, based on the total moles of the gaseous headspace material within the headspace.

5. The process as claimed in claim 3;
wherein the predetermined quality is defined as the molar concentration of diatomic (or molecular) oxygen, within the gaseous headspace material within the headspace of the photobioreactor, that is greater than, or equal to, 20 mol %, based on the total moles of the gaseous headspace material within the headspace.

6. The process as claimed in claim 3;
wherein the predetermined quality is defined as the ratio of the molar concentration of diatomic (or molecular) oxygen, within the gaseous headspace material within the headspace of the photobioreactor, to the molar concentration of carbon dioxide, within the gaseous headspace material within the headspace of the photobioreactor, that is greater than, or equal to, 20.

7. The process as claimed in claim 2;
wherein the discharging of the gaseous photobioreactor exhaust to the combustion zone of the combustor is effected in response to sensing of a predetermined quality that is suitable for effecting combustion of a fuel.

8. The process as claimed in claim 7;
wherein the predetermined quality is defined as the molar concentration of carbon dioxide, within the gaseous headspace material within the headspace of the photobioreactor, that is less than, or equal to, a predetermined maximum concentration.

9. The process as claimed in claim 7;
wherein the predetermined quality is defined as the molar concentration of diatomic (or molecular) oxygen, within the gaseous headspace material within the headspace of the photobioreactor, that is greater than, or equal to a predetermined minimum concentration.

10. The process as claimed in claim 7;
wherein the predetermined quality is defined as the ratio of the molar concentration of diatomic (or molecular) oxygen, within the gaseous headspace material within the headspace of the photobioreactor, to the molar concentration of carbon dioxide, within the gaseous headspace material within the headspace of the photobioreactor, that is greater than, or equal to, a predetermined minimum value.

11. The process as claimed in claim 1;
wherein the at least reducing the rate of supply of carbon dioxide to the reaction zone includes suspending the supply of carbon dioxide to the reaction zone, such that the supplying of carbon dioxide to the reaction zone is suspended, and the discharging at least a fraction of the gaseous headspace material to a space other than that of the combustion zone of the combustor is effected while the supplying of carbon dioxide to the reaction zone is suspended.

12. The process as claimed in claim 11;
wherein the discharging of the gaseous photobioreactor exhaust to the combustion zone of the combustor is effected when the gaseous headspace material, within the headspace, is of a predetermined quality that is suitable for effecting combustion of a fuel.

13. The process as claimed in claim 12;
wherein the predetermined quality is defined as the molar concentration of carbon dioxide, within the gaseous headspace material within the headspace of the photobioreactor, that is less than, or equal to, 1.0 mol %, based on the total moles of the gaseous headspace material within the headspace.

14. The process as claimed in claim 12;
wherein the predetermined quality is defined as the molar concentration of diatomic (or molecular) oxygen, within the gaseous headspace material within the headspace of the photobioreactor, that is greater than, or equal to, 20 mol %, based on the total moles of the gaseous headspace material within the headspace.

15. The process as claimed in claim 12;
wherein the predetermined quality is defined as the ratio of the molar concentration of diatomic (or molecular) oxygen, within the gaseous headspace material within the headspace of the photobioreactor, to the molar concentration of carbon dioxide, within the gaseous headspace material within the headspace of the photobioreactor, that is greater than, or equal to, 20.

16. The process as claimed in claim 11;
wherein the discharging of the gaseous photobioreactor exhaust to the combustion zone of the combustor is effected in response to sensing of a predetermined quality that is suitable for effecting combustion of a fuel.

17. The process as claimed in claim 16;
wherein the predetermined quality is defined as the molar concentration of carbon dioxide, within the gaseous headspace material within the headspace of the photobioreactor, that is less than, or equal to, a predetermined maximum concentration.

18. The process as claimed in claim 16;
wherein the predetermined quality is defined as the molar concentration of diatomic (or molecular) oxygen, within the gaseous headspace material within the headspace of the photobioreactor, that is greater than, or equal to a predetermined minimum concentration.

19. The process as claimed in claim 16;
wherein the predetermined quality is defined as the ratio of the molar concentration of diatomic (or molecular) oxygen, within the gaseous headspace material within the headspace of the photobioreactor, to the molar concentration of carbon dioxide, within the gaseous headspace material within the headspace of the photobioreactor, that is greater than, or equal to, a predetermined minimum value.

20. The process as claimed in claim 1;
wherein the at least reducing the rate of supply of carbon dioxide to the reaction zone of the photobioreactor is such that, after the reduction, carbon dioxide is being supplied to the reaction zone at a reduced molar rate.

\* \* \* \* \*